United States Patent
Lee et al.

(10) Patent No.: US 10,633,679 B2
(45) Date of Patent: Apr. 28, 2020

(54) MICROORGANISMS FOR PRODUCING DIAMINE AND PROCESS FOR PRODUCING DIAMINE USING THEM

(71) Applicant: CJ CHEILJEDANG CORPORATION, Seoul (KR)

(72) Inventors: Kyoung Min Lee, Seoul (KR); Su Jin Park, Seoul (KR); Hee Kyoung Jung, Seoul (KR); Young Lyeol Yang, Gyeonggi-do (KR); Hong Xian Li, Seoul (KR); Hye Won Um, Gyeonggi-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/306,755

(22) PCT Filed: Mar. 27, 2015

(86) PCT No.: PCT/KR2015/003065
§ 371 (c)(1),
(2) Date: Oct. 25, 2016

(87) PCT Pub. No.: WO2015/163591
PCT Pub. Date: Oct. 29, 2015

(65) Prior Publication Data
US 2017/0044581 A1    Feb. 16, 2017

(30) Foreign Application Priority Data
Apr. 25, 2014   (KR) .................. 10-2014-0049870

(51) Int. Cl.
| | | |
|---|---|---|
| *A61K 31/74* | (2006.01) | |
| *C12N 1/20* | (2006.01) | |
| *C12P 13/00* | (2006.01) | |
| *C07K 14/195* | (2006.01) | |
| *C07K 14/34* | (2006.01) | |
| *C12N 15/70* | (2006.01) | |
| *C12N 15/77* | (2006.01) | |

(52) U.S. Cl.
CPC .......... *C12P 13/001* (2013.01); *C07K 14/195* (2013.01); *C07K 14/34* (2013.01); *C12N 15/70* (2013.01); *C12N 15/77* (2013.01)

(58) Field of Classification Search
CPC .............................. C12P 13/02; C12P 13/0001
See application file for complete search history.

(56) References Cited

U.S. PATENT DOCUMENTS

2017/0044581 A1    2/2017   Lee et al.

FOREIGN PATENT DOCUMENTS

| CN | 103492553 A | 1/2014 |
|---|---|---|
| JP | 2009-531042 A | 9/2009 |
| JP | 2014-507152 A | 3/2014 |
| JP | 2016-514466 A | 5/2016 |
| KR | 10-0159812 B | 8/1998 |
| KR | 10-0620092 B | 8/2006 |
| KR | 1020120064046 A | 6/2012 |
| KR | 1020130082478 A | 7/2013 |
| KR | 101732788 B1 | 5/2017 |
| WO | 2006/005603 A1 | 1/2006 |
| WO | 2006/065095 A1 | 6/2006 |
| WO | 2009/096689 A2 | 8/2009 |
| WO | 2009/125924 A2 | 10/2009 |
| WO | 2009/125992 A2 | 10/2009 |
| WO | 2012/114256 A1 | 8/2012 |
| WO | 2013/093737 A1 | 6/2013 |
| WO | 2013/105827 A2 | 7/2013 |
| WO | 2014/148743 A1 | 9/2014 |

OTHER PUBLICATIONS

Igarashi and Kashiwagi, "Characteristics of cellular polyamine transport in prokaryotes and eukaryotes," Plant Physiology and Biochemistry 48: 506-512, 2010.
Kind et al., "Metabolic engineering of cellular transport for over-production of the platform chemical 1,5-diaminopentane in Corynebacterium glutamicum," Metabolic Engineering 13: 617-627, 2011.
NCBI Reference Sequence: WP_006769146.1, "membrane protein [*Corynebacterium efficiens*]," accessed May 26, 2013.
Qian et al., "Metabolic Engineering of *Escherichia coli* for the Production of Putrescine: A Four Carbon Diamine," Biotechnology and Bioengineering 104: 651-662, 2009.
Schneider et al., "Improving putrescine production by Corynebacterium glutamicum by fine-tuning ornithine transcarbamoylase activity using a plasmid addiction system," Appl. Microbiol. Biotechnol. 95: 169-178, 2012.
Schneider and Wendisch, "Putrescine production by engineered Corynebacterium glutamicum," Appl. Microbiol. Biotechnol. 88: 859-868, 2010.
Soksawatmaekhin et al., "Excretion and uptake of cadaverine by CadB and its physiological functions in *Escherichia coli*," Molecular Microbiology 51(5): 1401-1412, 2004.
Tomitori et al., "Multiple polyamine transport systems on the vacuolar membrane in yeast," Biochem. J. 353: 681-688, 2001.

(Continued)

*Primary Examiner* — Maryam Monshipouri
(74) *Attorney, Agent, or Firm* — Cooley LLP

(57) ABSTRACT

The present invention relates to a microorganism for producing diamine, in which activity of a protein having an amino acid sequence of SEQ ID NO: 6 or an amino acid sequence having 55% or higher sequence homology with SEQ ID NO: 6 is introduced or enhanced, and a method of producing diamine using the same.

7 Claims, No Drawings
Specification includes a Sequence Listing.

(56) References Cited

OTHER PUBLICATIONS

NCBI Reference Sequence NP_600742.1, histone acetyltransferase HPA2 and related acetyltransferase [Corynebacterium glutamicum ATCC 13032], dated Aug. 3, 2016, 2 pages.

Qian et al., "Metabolic Engineering of *Escherichia coli* for the Production of Cadaverine: A Five Carbon Diamine," Biotechnology and BioEngineering 108(1): 93-103, Jan. 1, 2011.

Database UniProtKB, [online], Accession No. C0XP92, <http://www.uniprot.org/uniprot/C0XP92.fasta?version=13>, Feb. 19, 2014 uploaded, [retrieved on Jul. 21, 2017], one page.

SEQUENCE LISTING

<160> NUMBER OF SEQ ID NOS: 34

<210> SEQ ID NO 1
<211> LENGTH: 25
<212> TYPE: DNA
<213> ORGANISM: Artificial Sequence
<220> FEATURE:
<223> OTHER INFORMATION: NCgl2522-del-F1_BamHI Primer

<400> SEQUENCE: 1
cgggatccca cgcctgtctg gtcgc                                          25

<210> SEQ ID NO 2
<211> LENGTH: 32
<212> TYPE: DNA
<213> ORGANISM: Artificial Sequence
<220> FEATURE:
<223> OTHER INFORMATION: NCgl2522-del-R1_SalI Primer

<400> SEQUENCE: 2
acgcgtcgac ggatcgtaac tgtaacgaat gg                                  32

<210> SEQ ID NO 3
<211> LENGTH: 29
<212> TYPE: DNA
<213> ORGANISM: Artificial Sequence
<220> FEATURE:
<223> OTHER INFORMATION: NCgl2522-del-F2_SalI Primer

<400> SEQUENCE: 3
acgcgtcgac cgcgtgcatc tttggacac                                      29

<210> SEQ ID NO 4
<211> LENGTH: 29
<212> TYPE: DNA
<213> ORGANISM: Artificial Sequence
<220> FEATURE:
<223> OTHER INFORMATION: NCgl2522-del-R2_XbaI Primer

<400> SEQUENCE: 4
ctagtctaga gagctgcacc aggtagacg                                      29

<210> SEQ ID NO 5

<211> LENGTH: 1440
<212> TYPE: DNA
<213> ORGANISM: Corynebacterium efficiens

<400> SEQUENCE: 5

```
atgaatccca cagcctcgca acgttggacc ttcctggccg tgatcagcgc tggcctgttt      60
ctcatcggcg tggataattc cattctctat acggcgctgc cggtgttgcg ggaggaactg     120
caggccaccg agctgcaggg gctgtggatc atcaatgcct accccctgat gctggctggc     180
ctgctgctgg gtacgggcac gctcggggac aagatcgggc accgtctgat gttcctcacc     240
ggactggcgg tctttggcgt ggcctccctg gccgccgcct tctccccaac ggcatgggtg     300
ctggtggccc gcgcgccctt gctggggatc ggtgcgcgcg cgatgatgcc cgccacactc     360
gcactgatcc ggatcacctt tgaggatgag cgggagagaa ataccgccat cggcatctgg     420
ggatcggtgg cgctcgcggg tgcggcggcc ggcccggttc tcggcggtgt gctgcttgag     480
ttcttctggt ggggttcggt gttcctgatc aatgtgccgg tggttctgat agcactcgtc     540
ctcaccctgc tggtcgcccc gcccaatatg cccaacccgg acaaacactg ggatgcgctc     600
tcctcggtgt atgcgctcct ggccctgacc ggtctggtca tggcgatcaa ggaggccgtg     660
tcccccaccg gcagctctg gctgctcgcg gtggtggttg ccgttgtggg tgcggtgctg     720
ttccagcgtc gacaggcgtc acagccggaa cccctcctgg acttctcgct cttccgcaac     780
cgcctgttca ccggtggcgt gatcgcgcc ggcctggcca tgtttgtggt tgccggcctg     840
gagatgacca ccacgcagcg cttccagctg tccgcggggt tcagcccct ggaggccggc     900
ttcctgatga cggcgctggc ggcggcgagc atcccgatgt cggtcatcgg tggtgccaac     960
ctacaccgct ggggcttcct gccgctgatc agcggtggtt tcctcagcgc gacggtcggt    1020
gtcgccctga tcatctgggc gctggatgtg agcctgatcc cctggtcgt gggcctggtg    1080
ctcgtcggcc tcggcagcgg cgccacgatc tctgtcgcct ccaccgccat catcgggtcc    1140
gcgccggtcc gcaaggccgg gatggccgcc tccatcgagg aggtgtccta cgagttcggc    1200
acgttgtgct ccgtggcgat cctcggcagc ctcttccccg cgttctacgc cctctccgca    1260
ccggccgagg tggccgacag tttcgccacc ggggtggatc atgcggtgtt cggcgaggcc    1320
gccccgcgccg cgctggactc ggcctatgtc aacgtcctgt tcatcgccct cggtgtggcc    1380
ctggtgacca ccttcatcac cgcgtggtgc ttccgcgaca accccgaagcg ccccgggtga    1440
```

<210> SEQ ID NO 6
<211> LENGTH: 479
<212> TYPE: PRT
<213> ORGANISM: Corynebacterium efficiens

<400> SEQUENCE: 6

```
Met Asn Pro Thr Ala Ser Gln Arg Trp Thr Phe Leu Ala Val Ile Ser
1               5                   10                  15

Ala Gly Leu Phe Leu Ile Gly Val Asp Asn Ser Ile Leu Tyr Thr Ala
            20                  25                  30

Leu Pro Val Leu Arg Glu Glu Leu Gln Ala Thr Glu Leu Gln Gly Leu
        35                  40                  45

Trp Ile Ile Asn Ala Tyr Pro Leu Met Leu Ala Gly Leu Leu Leu Gly
    50                  55                  60

Thr Gly Thr Leu Gly Asp Lys Ile Gly His Arg Leu Met Phe Leu Thr
65                  70                  75                  80

Gly Leu Ala Val Phe Gly Val Ala Ser Leu Ala Ala Ala Phe Ser Pro
                85                  90                  95
```

Thr Ala Trp Val Leu Val Ala Ala Arg Ala Leu Leu Gly Ile Gly Ala
              100                 105                 110

Ala Ala Met Met Pro Ala Thr Leu Ala Leu Ile Arg Ile Thr Phe Glu
              115                 120                 125

Asp Glu Arg Glu Arg Asn Thr Ala Ile Gly Ile Trp Gly Ser Val Ala
130                 135                 140

Leu Ala Gly Ala Ala Gly Pro Val Leu Gly Gly Val Leu Leu Glu
145                 150                 155                 160

Phe Phe Trp Trp Gly Ser Val Phe Leu Ile Asn Val Pro Val Val Leu
                165                 170                 175

Ile Ala Leu Val Leu Thr Leu Leu Val Ala Pro Pro Asn Met Pro Asn
              180                 185                 190

Pro Asp Lys His Trp Asp Ala Leu Ser Ser Val Tyr Ala Leu Leu Ala
              195                 200                 205

Leu Thr Gly Leu Val Met Ala Ile Lys Glu Ala Val Ser Pro Thr Gly
              210                 215                 220

Gln Leu Trp Leu Leu Ala Val Val Val Ala Val Val Gly Ala Val Leu
225                 230                 235                 240

Phe Gln Arg Arg Gln Ala Ser Gln Pro Glu Pro Leu Leu Asp Phe Ser
              245                 250                 255

Leu Phe Arg Asn Arg Leu Phe Thr Gly Gly Val Ile Ala Ala Gly Leu
              260                 265                 270

Ala Met Phe Val Val Ala Gly Leu Glu Met Thr Thr Thr Gln Arg Phe
              275                 280                 285

Gln Leu Ser Ala Gly Phe Ser Pro Leu Glu Ala Gly Phe Leu Met Thr
              290                 295                 300

Ala Leu Ala Ala Ala Ser Ile Pro Met Ser Val Ile Gly Gly Ala Asn
305                 310                 315                 320

Leu His Arg Trp Gly Phe Leu Pro Leu Ile Ser Gly Gly Phe Leu Ser
              325                 330                 335

Ala Thr Val Gly Val Ala Leu Ile Ile Trp Ala Leu Asp Val Ser Leu
              340                 345                 350

Ile Pro Leu Val Val Gly Leu Val Leu Val Gly Leu Gly Ser Gly Ala
              355                 360                 365

Thr Ile Ser Val Ala Ser Thr Ala Ile Ile Gly Ser Ala Pro Val Arg
              370                 375                 380

Lys Ala Gly Met Ala Ala Ser Ile Glu Glu Val Ser Tyr Glu Phe Gly
385                 390                 395                 400

Thr Leu Cys Ser Val Ala Ile Leu Gly Ser Leu Phe Pro Ala Phe Tyr
              405                 410                 415

Ala Leu Ser Ala Pro Ala Glu Val Ala Asp Ser Phe Ala Thr Gly Val
              420                 425                 430

Asp His Ala Val Phe Gly Glu Ala Ala Arg Ala Ala Leu Asp Ser Ala
              435                 440                 445

Tyr Val Asn Val Leu Phe Ile Ala Leu Gly Val Ala Leu Val Thr Thr
              450                 455                 460

Phe Ile Thr Ala Trp Cys Phe Arg Asp Asn Pro Lys Arg Pro Gly
465                 470                 475

<210> SEQ ID NO 7
<211> LENGTH: 40
<212> TYPE: DNA
<213> ORGANISM: Artificial Sequence
<220> FEATURE:

<223> OTHER INFORMATION: CJ7-Forward Primer

<400> SEQUENCE: 7
tgtcgggccc actagtagaa acatcccagc gctactaata                                40

<210> SEQ ID NO 8
<211> LENGTH: 23
<212> TYPE: DNA
<213> ORGANISM: Artificial Sequence
<220> FEATURE:
<223> OTHER INFORMATION: CJ7-Reverse Primer

<400> SEQUENCE: 8
agtgtttcct ttcgttgggt acg                                                 23

<210> SEQ ID NO 9
<211> LENGTH: 36
<212> TYPE: DNA
<213> ORGANISM: Artificial Sequence
<220> FEATURE:
<223> OTHER INFORMATION: CE2495-Forward Primer

<400> SEQUENCE: 9
caacgaaagg aaacactatg aatcccacag cctcgc                                   36

<210> SEQ ID NO 10
<211> LENGTH: 33
<212> TYPE: DNA
<213> ORGANISM: Artificial Sequence
<220> FEATURE:
<223> OTHER INFORMATION: CE2495-Reverse Primer

<400> SEQUENCE: 10
gaatgagttc ctcgagtcac ccggggcgct tcg                                      33

<210> SEQ ID NO 11
<211> LENGTH: 203
<212> TYPE: PRT
<213> ORGANISM: Corynebacterium glutamicum
<220> FEATURE:
<221> NAME/KEY: MISC_FEATURE
<222> LOCATION: (1)..(203)
<223> OTHER INFORMATION: NCgl1469

<400> SEQUENCE: 11

Met Ser Pro Thr Val Leu Pro Ala Thr Gln Ala Asp Phe Pro Lys Ile
1               5                  10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala

```
                  130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                    165                 170                 175

Val Pro Leu Gly Tyr Ile Pro Ser Asp Asp Asp Gly Thr Pro Glu Leu
                180                 185                 190

Ala Met Trp Lys Pro Pro Ala Met Pro Thr Val
                195                 200

<210> SEQ ID NO 12
<211> LENGTH: 203
<212> TYPE: PRT
<213> ORGANISM: Corynebacterium glutamicum
<220> FEATURE:
<221> NAME/KEY: MISC_FEATURE
<222> LOCATION: (1)..(203)
<223> OTHER INFORMATION: NCgl1469

<400> SEQUENCE: 12

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
                20                  25                  30

Trp Ile Pro Gln Pro Asp Pro Gly Ser Ala Lys Leu Arg Ala Leu Phe
            35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Ile Leu Pro Arg
                85                  90                  95

Leu Val Ser Ile Phe Gly Ile Lys Ala Ala Gln Val Ala Trp Thr Asp
                100                 105                 110

Leu Ser Ser Ala Arg Phe His Pro Lys Phe Pro His Trp Tyr Leu Tyr
            115                 120                 125

Thr Val Ala Thr Ser Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160

Glu Ala Thr Ser Thr Arg Ala Ala Gln Leu Tyr Asn Arg Leu Gly Phe
                    165                 170                 175

Val Pro Leu Gly Tyr Ile Pro Ser Asp Asp Asp Gly Thr Pro Glu Leu
                180                 185                 190

Ala Met Trp Lys Pro Pro Ala Met Pro Thr Val
                195                 200

<210> SEQ ID NO 13
<211> LENGTH: 186
<212> TYPE: PRT
<213> ORGANISM: Escherichia Coli
<220> FEATURE:
<221> NAME/KEY: MISC_FEATURE
<222> LOCATION: (1)..(186)
<223> OTHER INFORMATION: SpeG (E.coli) W3110

<400> SEQUENCE: 13

Met Pro Ser Ala His Ser Val Lys Leu Arg Pro Leu Glu Arg Glu Asp
1               5                   10                  15
```

Leu Arg Tyr Val His Gln Leu Asp Asn Asn Ala Ser Val Met Arg Tyr
            20                  25                  30

Trp Phe Glu Glu Pro Tyr Glu Ala Phe Val Glu Leu Ser Asp Leu Tyr
        35                  40                  45

Asp Lys His Ile His Asp Gln Ser Glu Arg Arg Phe Val Glu Cys
50                  55                  60

Asp Gly Glu Lys Ala Gly Leu Val Glu Leu Val Glu Ile Asn His Val
65                  70                  75                  80

His Arg Arg Ala Glu Phe Gln Ile Ile Ile Ser Pro Glu Tyr Gln Gly
                85                  90                  95

Lys Gly Leu Ala Thr Arg Ala Ala Lys Leu Ala Met Asp Tyr Gly Phe
            100                 105                 110

Thr Val Leu Asn Leu Tyr Lys Leu Tyr Leu Ile Val Asp Lys Glu Asn
            115                 120                 125

Glu Lys Ala Ile His Ile Tyr Arg Lys Leu Gly Phe Ser Val Glu Gly
130                 135                 140

Glu Leu Met His Glu Phe Phe Ile Asn Gly Gln Tyr Arg Asn Ala Ile
145                 150                 155                 160

Arg Met Cys Ile Phe Gln His Gln Tyr Leu Ala Glu His Lys Thr Pro
                165                 170                 175

Gly Gln Thr Leu Leu Lys Pro Thr Ala Gln
            180                 185

<210> SEQ ID NO 14
<211> LENGTH: 357
<212> TYPE: PRT
<213> ORGANISM: Corynebacterium glutamicum
<220> FEATURE:
<221> NAME/KEY: MISC_FEATURE
<222> LOCATION: (1)..(357)
<223> OTHER INFORMATION: Acetyl gamma glutamyl phosphate reductase
      (ArgC)

<400> SEQUENCE: 14

Met Ile Met His Asn Val Tyr Gly Val Thr Met Thr Ile Lys Val Ala
1               5                   10                  15

Ile Ala Gly Ala Ser Gly Tyr Ala Gly Gly Glu Ile Leu Arg Leu Leu
            20                  25                  30

Leu Gly His Pro Ala Tyr Ala Ser Gly Glu Leu Glu Ile Gly Ala Leu
        35                  40                  45

Thr Ala Ala Ser Thr Ala Gly Ser Thr Leu Gly Glu Leu Met Pro His
50                  55                  60

Ile Pro Gln Leu Ala Asp Arg Val Ile Gln Asp Thr Thr Ala Glu Thr
65                  70                  75                  80

Leu Ala Gly His Asp Val Val Phe Leu Gly Leu Pro His Gly Phe Ser
                85                  90                  95

Ala Glu Ile Ala Leu Gln Leu Gly Pro Asp Val Thr Val Ile Asp Cys
            100                 105                 110

Ala Ala Asp Phe Arg Leu Gln Asn Ala Ala Asp Trp Glu Lys Phe Tyr
            115                 120                 125

Gly Ser Glu His Gln Gly Thr Trp Pro Tyr Gly Ile Pro Glu Met Pro
130                 135                 140

Gly His Arg Glu Ala Leu Arg Gly Ala Lys Arg Val Ala Val Pro Gly
145                 150                 155                 160

Cys Phe Pro Thr Gly Ala Thr Leu Ala Leu Leu Pro Ala Val Gln Ala
                165                 170                 175

```
Gly Leu Ile Glu Pro Asp Val Ser Val Ser Ile Thr Gly Val Ser
                180             185                 190
Gly Ala Gly Lys Lys Ala Ser Val Ala Leu Leu Gly Ser Glu Thr Met
            195                 200             205
Gly Ser Leu Lys Ala Tyr Asn Thr Ser Gly Lys His Arg His Thr Pro
    210                 215                 220
Glu Ile Ala Gln Asn Leu Gly Glu Val Ser Asp Lys Pro Val Lys Val
225                 230                 235                 240
Ser Phe Thr Pro Val Leu Ala Pro Leu Pro Arg Gly Ile Leu Thr Thr
                245                 250                 255
Ala Thr Ala Pro Leu Lys Glu Gly Val Thr Ala Glu Gln Ala Arg Ala
            260                 265                 270
Val Tyr Glu Glu Phe Tyr Ala Gln Glu Thr Phe Val His Val Leu Pro
        275                 280                 285
Glu Gly Ala Gln Pro Gln Thr Gln Ala Val Leu Gly Ser Asn Met Cys
    290                 295                 300
His Val Gln Val Glu Ile Asp Glu Glu Ala Gly Lys Val Leu Val Thr
305                 310                 315                 320
Ser Ala Ile Asp Asn Leu Thr Lys Gly Thr Ala Gly Ala Ala Val Gln
                325                 330                 335
Cys Met Asn Leu Ser Val Gly Phe Asp Glu Ala Ala Gly Leu Pro Gln
            340                 345                 350
Val Gly Val Ala Pro
            355

<210> SEQ ID NO 15
<211> LENGTH: 388
<212> TYPE: PRT
<213> ORGANISM: Corynebacterium glutamicum
<220> FEATURE:
<221> NAME/KEY: MISC_FEATURE
<222> LOCATION: (1)..(388)
<223> OTHER INFORMATION: Acetyl glutamate synthase or Ornithine acetyl
      transferase (ArgJ)

<400> SEQUENCE: 15

Met Ala Glu Lys Gly Ile Thr Ala Pro Lys Gly Phe Val Ala Ser Ala
1               5                   10                  15
Thr Thr Ala Gly Ile Lys Ala Ser Gly Asn Pro Asp Met Ala Leu Val
            20                  25                  30
Val Asn Gln Gly Pro Glu Phe Ser Ala Ala Val Phe Thr Arg Asn
        35                  40                  45
Arg Val Phe Ala Ala Pro Val Lys Val Ser Arg Glu Asn Val Ala Asp
    50                  55                  60
Gly Gln Ile Arg Ala Val Leu Tyr Asn Ala Gly Ala Asn Ala Cys
65                  70                  75                  80
Asn Gly Leu Gln Gly Glu Lys Asp Ala Arg Glu Ser Val Ser His Leu
                85                  90                  95
Ala Gln Asn Leu Gly Leu Glu Asp Ser Asp Ile Gly Val Cys Ser Thr
            100                 105                 110
Gly Leu Ile Gly Glu Leu Leu Pro Met Asp Lys Leu Asn Ala Gly Ile
        115                 120                 125
Asp Gln Leu Thr Ala Glu Gly Ala Leu Gly Asp Asn Gly Ala Ala Ala
    130                 135                 140
Ala Lys Ala Ile Met Thr Thr Asp Thr Val Asp Lys Glu Thr Val Val
145                 150                 155                 160
```

Phe Ala Asp Gly Trp Thr Val Gly Gly Met Gly Lys Gly Val Gly Met
                165                 170                 175

Met Ala Pro Ser Leu Ala Thr Met Leu Val Cys Leu Thr Thr Asp Ala
                180                 185                 190

Ser Val Thr Gln Glu Met Ala Gln Ile Ala Leu Ala Asn Ala Thr Ala
                195                 200                 205

Val Thr Phe Asp Thr Leu Asp Ile Asp Gly Ser Thr Ser Thr Asn Asp
            210                 215                 220

Thr Val Phe Leu Leu Ala Ser Gly Ala Ser Gly Ile Thr Pro Thr Gln
225                 230                 235                 240

Asp Glu Leu Asn Asp Ala Val Tyr Ala Ala Cys Ser Asp Ile Ala Ala
                245                 250                 255

Lys Leu Gln Ala Asp Ala Glu Gly Val Thr Lys Arg Val Ala Val Thr
                260                 265                 270

Val Val Gly Thr Thr Asn Asn Glu Gln Ala Ile Asn Ala Ala Arg Thr
            275                 280                 285

Val Ala Arg Asp Asn Leu Phe Lys Cys Ala Met Phe Gly Ser Asp Pro
            290                 295                 300

Asn Trp Gly Arg Val Leu Ala Ala Val Gly Met Ala Ser Ala Asp Met
305                 310                 315                 320

Glu Pro Glu Lys Ile Ser Val Phe Phe Asn Gly Gln Ala Val Cys Leu
                325                 330                 335

Asp Ser Thr Gly Ala Pro Gly Ala Arg Glu Val Asp Leu Ser Gly Ala
            340                 345                 350

Asp Ile Asp Val Arg Ile Asp Leu Gly Thr Ser Gly Glu Gly Gln Ala
            355                 360                 365

Thr Val Arg Thr Thr Asp Leu Ser Phe Ser Tyr Val Glu Ile Asn Ser
        370                 375                 380

Ala Tyr Ser Ser
385

<210> SEQ ID NO 16
<211> LENGTH: 317
<212> TYPE: PRT
<213> ORGANISM: Corynebacterium sp.
<220> FEATURE:
<221> NAME/KEY: MISC_FEATURE
<222> LOCATION: (1)..(317)
<223> OTHER INFORMATION: Acetyl glutamate kinase (ArgB)

<400> SEQUENCE: 16

Met Asn Asp Leu Ile Lys Asp Leu Gly Ser Glu Val Arg Ala Asn Val
1               5                   10                  15

Leu Ala Glu Ala Leu Pro Trp Leu Gln His Phe Arg Asp Lys Ile Val
            20                  25                  30

Val Val Lys Tyr Gly Gly Asn Ala Met Val Asp Asp Leu Lys Ala
            35                  40                  45

Ala Phe Ala Ala Asp Met Val Phe Leu Arg Thr Val Gly Ala Lys Pro
        50                  55                  60

Val Val His Gly Gly Gly Pro Gln Ile Ser Glu Met Leu Asn Arg
65                  70                  75                  80

Val Gly Leu Gln Gly Glu Phe Lys Gly Gly Phe Arg Val Thr Thr Pro
                85                  90                  95

Glu Val Met Asp Ile Val Arg Met Val Leu Phe Gly Gln Val Gly Arg
            100                 105                 110

```
Asp Leu Val Gly Leu Ile Asn Ser His Gly Pro Tyr Ala Val Gly Thr
            115                 120                 125

Ser Gly Glu Asp Ala Gly Leu Phe Thr Ala Gln Lys Arg Met Val Asn
        130                 135                 140

Ile Asp Gly Val Pro Thr Asp Ile Gly Leu Val Gly Asp Ile Ile Asn
145                 150                 155                 160

Val Asp Ala Ser Ser Leu Met Asp Ile Ile Glu Ala Gly Arg Ile Pro
                165                 170                 175

Val Val Ser Thr Ile Ala Pro Gly Glu Asp Gly Gln Ile Tyr Asn Ile
            180                 185                 190

Asn Ala Asp Thr Ala Ala Gly Ala Leu Ala Ala Ile Gly Ala Glu
        195                 200                 205

Arg Leu Leu Val Leu Thr Asn Val Glu Gly Leu Tyr Thr Asp Trp Pro
210                 215                 220

Asp Lys Ser Ser Leu Val Ser Lys Ile Lys Ala Thr Glu Leu Glu Ala
225                 230                 235                 240

Ile Leu Pro Gly Leu Asp Ser Gly Met Ile Pro Lys Met Glu Ser Cys
                245                 250                 255

Leu Asn Ala Val Arg Gly Gly Val Ser Ala Ala His Val Ile Asp Gly
            260                 265                 270

Arg Ile Ala His Ser Val Leu Leu Glu Leu Leu Thr Met Gly Gly Ile
        275                 280                 285

Gly Thr Met Val Leu Pro Asp Val Phe Asp Arg Glu Asn Tyr Pro Glu
290                 295                 300

Gly Thr Val Phe Arg Lys Asp Lys Asp Gly Glu Leu
305                 310                 315

<210> SEQ ID NO 17
<211> LENGTH: 391
<212> TYPE: PRT
<213> ORGANISM: Corynebacterium glutamicum
<220> FEATURE:
<221> NAME/KEY: MISC_FEATURE
<222> LOCATION: (1)..(391)
<223> OTHER INFORMATION: Acetyl ornithine aminotransferase (ArgD)

<400> SEQUENCE: 17

Met Ser Thr Leu Glu Thr Trp Pro Gln Val Ile Ile Asn Thr Tyr Gly
1               5                   10                  15

Thr Pro Pro Val Glu Leu Val Ser Gly Lys Gly Ala Thr Val Thr Asp
            20                  25                  30

Asp Gln Gly Asn Val Tyr Ile Asp Leu Leu Ala Gly Ile Ala Val Asn
        35                  40                  45

Ala Leu Gly His Ala His Pro Ala Ile Ile Glu Ala Val Thr Asn Gln
    50                  55                  60

Ile Gly Gln Leu Gly His Val Ser Asn Leu Phe Ala Ser Arg Pro Val
65                  70                  75                  80

Val Glu Val Ala Glu Glu Leu Ile Lys Arg Phe Ser Leu Asp Asp Ala
                85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
130                 135                 140

Ala Leu Thr Gly Gln Pro Asp Lys Arg Glu Ala Phe Leu Pro Met Pro
```

```
                145                 150                 155                 160
        Ser Gly Val Glu Phe Tyr Pro Tyr Gly Asp Thr Asp Tyr Leu Arg Lys
                        165                 170                 175

Met Val Glu Thr Asn Pro Thr Asp Val Ala Ala Ile Phe Leu Glu Pro
                        180                 185                 190

Ile Gln Gly Glu Thr Gly Val Pro Ala Pro Glu Gly Phe Leu Lys
                        195                 200                 205

Ala Val Arg Glu Leu Cys Asp Glu Tyr Gly Ile Leu Met Ile Thr Asp
                210                 215                 220

Glu Val Gln Thr Gly Val Gly Arg Thr Gly Asp Phe Phe Ala His Gln
        225                 230                 235                 240

His Asp Gly Val Val Pro Asp Val Val Thr Met Ala Lys Gly Leu Gly
                        245                 250                 255

Gly Gly Leu Pro Ile Gly Ala Cys Leu Ala Thr Gly Arg Ala Ala Glu
                        260                 265                 270

Leu Met Thr Pro Gly Lys His Gly Thr Thr Phe Gly Gly Asn Pro Val
                        275                 280                 285

Ala Cys Ala Ala Ala Lys Ala Val Leu Ser Val Val Asp Asp Ala Phe
                        290                 295                 300

Cys Ala Glu Val Ala Arg Lys Gly Glu Leu Phe Lys Glu Leu Leu Ala
        305                 310                 315                 320

Lys Val Asp Gly Val Asp Val Arg Gly Arg Gly Leu Met Leu Gly
                        325                 330                 335

Val Val Leu Glu Arg Asp Val Ala Lys Gln Ala Val Leu Asp Gly Phe
                        340                 345                 350

Lys His Gly Val Ile Leu Asn Ala Pro Ala Asp Asn Ile Ile Arg Leu
                        355                 360                 365

Thr Pro Pro Leu Val Ile Thr Asp Glu Glu Ile Ala Asp Ala Val Lys
                        370                 375                 380

Ala Ile Ala Glu Thr Ile Ala
        385                 390

<210> SEQ ID NO 18
<211> LENGTH: 319
<212> TYPE: PRT
<213> ORGANISM: Corynebacterium glutamicum
<220> FEATURE:
<221> NAME/KEY: MISC_FEATURE
<222> LOCATION: (1)..(319)
<223> OTHER INFORMATION: Ornithine carbamoyl transferase (argF)

<400> SEQUENCE: 18

Met Thr Ser Gln Pro Gln Val Arg His Phe Leu Ala Asp Asp Leu
        1               5                   10                  15

Thr Pro Ala Glu Gln Ala Glu Val Leu Thr Leu Ala Ala Lys Leu Lys
                        20                  25                  30

Ala Ala Pro Phe Ser Glu Arg Pro Leu Glu Gly Pro Lys Ser Val Ala
                        35                  40                  45

Val Leu Phe Asp Lys Thr Ser Thr Arg Thr Arg Phe Ser Phe Asp Ala
                50                  55                  60

Gly Ile Ala His Leu Gly Gly His Ala Ile Val Val Asp Ser Gly Ser
        65                  70                  75                  80

Ser Gln Met Gly Lys Gly Glu Ser Leu Gln Asp Thr Ala Ala Val Leu
                        85                  90                  95

Ser Arg Tyr Val Glu Ala Ile Val Trp Arg Thr Tyr Ala His Ser Asn
                        100                 105                 110
```

Phe His Ala Met Ala Glu Thr Ser Thr Val Pro Leu Val Asn Ser Leu
            115                 120                 125

Ser Asp Asp Leu His Pro Cys Gln Ile Leu Ala Asp Leu Gln Thr Ile
    130                 135                 140

Val Glu Asn Leu Ser Pro Glu Glu Gly Pro Ala Gly Leu Lys Gly Lys
145                 150                 155                 160

Lys Ala Val Tyr Leu Gly Asp Gly Asp Asn Asn Met Ala Asn Ser Tyr
                165                 170                 175

Met Ile Gly Phe Ala Thr Ala Gly Met Asp Ile Ser Ile Ile Ala Pro
            180                 185                 190

Glu Gly Phe Gln Pro Arg Ala Glu Phe Val Arg Ala Glu Lys Arg
            195                 200                 205

Gly Gln Glu Thr Gly Ala Lys Val Val Thr Asp Ser Leu Asp Glu
    210                 215                 220

Val Ala Gly Ala Asp Val Val Ile Thr Asp Thr Trp Val Ser Met Gly
225                 230                 235                 240

Met Glu Asn Asp Gly Ile Asp Arg Thr Thr Pro Phe Val Pro Tyr Gln
                245                 250                 255

Val Asn Asp Glu Val Met Ala Lys Ala Asn Asp Gly Ala Ile Phe Leu
            260                 265                 270

His Cys Leu Pro Ala Tyr Arg Gly Lys Glu Val Ala Ala Ser Val Ile
            275                 280                 285

Asp Gly Pro Ala Ser Lys Val Phe Asp Glu Ala Glu Asn Arg Leu His
    290                 295                 300

Ala Gln Lys Ala Leu Leu Val Trp Leu Leu Ala Asn Gln Pro Arg
305                 310                 315

<210> SEQ ID NO 19
<211> LENGTH: 533
<212> TYPE: PRT
<213> ORGANISM: Corynebacterium glutamicum
<220> FEATURE:
<221> NAME/KEY: MISC_FEATURE
<222> LOCATION: (1)..(533)
<223> OTHER INFORMATION: Glutamate expoter (NCgl1221)

<400> SEQUENCE: 19

Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Arg
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

-continued

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
            165                 170                 175

Cys Ile Asn Asn Ser Asn Asn Trp Ser Arg Ala Val Val Ile Pro
        180                 185                 190

Ile Pro Met Leu Gly Ser Glu Asn Ile Thr Asp Val Ile Ala Arg Ser
        195                 200                 205

Glu Ala Thr Arg Arg Ala Leu Gly Gln Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
                260                 265                 270

Ile Ile Ser Glu Phe Trp Glu Glu Tyr Gly Ser Ala Thr Thr Thr Ser
                275                 280                 285

Gly Thr Leu Ile Asp Ser Leu His Val Glu His Glu Pro Lys Thr
    290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Val Ile Asn Ala Gly Asn Pro Glu Lys Glu
            340                 345                 350

Leu Asp Ser Asp Val Leu Glu Gln Glu Leu Ser Ser Glu Pro Glu
            355                 360                 365

Glu Thr Ala Lys Pro Asp His Ser Leu Arg Gly Phe Phe Arg Thr Asp
    370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Val Met Thr Val Glu Pro Ser Glu Asn Trp Gln Asn Ser Ser
        420                 425                 430

Gly Trp Leu Ser Pro Ser Thr Ala Thr Ser Thr Ala Val Thr Thr Ser
            435                 440                 445

Glu Thr Ser Ala Pro Val Ser Thr Pro Ser Met Thr Val Pro Thr Thr
    450                 455                 460

Val Glu Glu Thr Pro Thr Met Glu Ser Asn Val Glu Thr Gln Gln Glu
465                 470                 475                 480

Thr Ser Thr Pro Ala Thr Ala Thr Pro Gln Arg Ala Asp Thr Ile Glu
                485                 490                 495

Pro Thr Glu Glu Ala Thr Ser Gln Glu Glu Thr Thr Ala Ser Gln Thr
            500                 505                 510

Gln Ser Pro Ala Val Glu Ala Pro Thr Ala Val Gln Glu Thr Val Ala
            515                 520                 525

Pro Thr Ser Thr Pro
        530

<210> SEQ ID NO 20
<211> LENGTH: 711
<212> TYPE: PRT

<210> ORGANISM: Unknown
<220> FEATURE:
<223> OTHER INFORMATION: Multispecies proteobacteria ornithine decarboxylase (ODC) protein sequence

<400> SEQUENCE: 20

```
Met Lys Ser Met Asn Ile Ala Ala Ser Ser Glu Leu Val Ser Arg Leu
1               5                   10                  15
Ser Ser His Arg Arg Val Val Ala Leu Gly Asp Thr Asp Phe Thr Asp
                20                  25                  30
Val Ala Ala Val Val Ile Thr Ala Ala Asp Ser Arg Ser Gly Ile Leu
            35                  40                  45
Ala Leu Leu Lys Arg Thr Gly Phe His Leu Pro Val Phe Leu Tyr Ser
        50                  55                  60
Glu His Ala Val Glu Leu Pro Ala Gly Val Thr Ala Val Ile Asn Gly
65                  70                  75                  80
Asn Glu Gln Gln Trp Leu Glu Leu Glu Ser Ala Ala Cys Gln Tyr Glu
                85                  90                  95
Glu Asn Leu Leu Pro Pro Phe Tyr Asp Thr Leu Thr Gln Tyr Val Glu
                100                 105                 110
Met Gly Asn Ser Thr Phe Ala Cys Pro Gly His Gln His Gly Ala Phe
            115                 120                 125
Phe Lys Lys His Pro Ala Gly Arg His Phe Tyr Asp Phe Phe Gly Glu
        130                 135                 140
Asn Val Phe Arg Ala Asp Met Cys Asn Ala Asp Val Lys Leu Gly Asp
145                 150                 155                 160
Leu Leu Ile His Glu Gly Ser Ala Lys Asp Ala Gln Lys Phe Ala Ala
                165                 170                 175
Lys Val Phe His Ala Asp Lys Thr Tyr Phe Val Leu Asn Gly Thr Ser
            180                 185                 190
Ala Ala Asn Lys Val Val Thr Asn Ala Leu Leu Thr Arg Gly Asp Leu
        195                 200                 205
Val Leu Phe Asp Arg Asn Asn His Lys Ser Asn His His Gly Ala Leu
    210                 215                 220
Ile Gln Ala Gly Ala Thr Pro Val Tyr Leu Glu Ala Ser Arg Asn Pro
225                 230                 235                 240
Phe Gly Phe Ile Gly Gly Ile Asp Ala His Cys Phe Asn Glu Glu Tyr
                245                 250                 255
Leu Arg Gln Gln Ile Arg Asp Val Ala Pro Glu Lys Ala Asp Leu Pro
            260                 265                 270
Arg Pro Tyr Arg Leu Ala Ile Ile Gln Leu Gly Thr Tyr Asp Gly Thr
        275                 280                 285
Val Tyr Asn Ala Arg Gln Val Ile Asp Thr Val Gly His Leu Cys Asp
    290                 295                 300
Tyr Ile Leu Phe Asp Ser Ala Trp Val Gly Tyr Glu Gln Phe Ile Pro
305                 310                 315                 320
Met Met Ala Asp Ser Ser Pro Leu Leu Leu Glu Leu Asn Glu Asn Asp
                325                 330                 335
Pro Gly Ile Phe Val Thr Gln Ser Val His Lys Gln Gln Ala Gly Phe
            340                 345                 350
Ser Gln Thr Ser Gln Ile His Lys Lys Asp Asn His Ile Arg Gly Gln
        355                 360                 365
Ala Arg Phe Cys Pro His Lys Arg Leu Asn Asn Ala Phe Met Leu His
    370                 375                 380
```

```
Ala Ser Thr Ser Pro Phe Tyr Pro Leu Phe Ala Ala Leu Asp Val Asn
385                 390                 395                 400

Ala Lys Ile His Glu Gly Glu Ser Gly Arg Arg Leu Trp Ala Glu Cys
            405                 410                 415

Val Glu Ile Gly Ile Glu Ala Arg Lys Ala Ile Leu Ala Arg Cys Lys
            420                 425                 430

Leu Phe Arg Pro Phe Ile Pro Pro Val Val Asp Gly Lys Leu Trp Gln
        435                 440                 445

Asp Tyr Pro Thr Ser Val Leu Ala Ser Asp Arg Arg Phe Phe Ser Phe
    450                 455                 460

Glu Pro Gly Ala Lys Trp His Gly Phe Glu Gly Tyr Ala Ala Asp Gln
465                 470                 475                 480

Tyr Phe Val Asp Pro Cys Lys Leu Leu Leu Thr Thr Pro Gly Ile Asp
            485                 490                 495

Ala Glu Thr Gly Glu Tyr Ser Asp Phe Gly Val Pro Ala Thr Ile Leu
            500                 505                 510

Ala His Tyr Leu Arg Glu Asn Gly Ile Val Pro Glu Lys Cys Asp Leu
        515                 520                 525

Asn Ser Ile Leu Phe Leu Leu Thr Pro Ala Glu Ser His Glu Lys Leu
530                 535                 540

Ala Gln Leu Val Ala Met Leu Ala Gln Phe Glu Gln His Ile Glu Asp
545                 550                 555                 560

Asp Ser Pro Leu Val Glu Val Leu Pro Ser Val Tyr Asn Lys Tyr Pro
            565                 570                 575

Val Arg Tyr Arg Asp Tyr Thr Leu Arg Gln Leu Cys Gln Glu Met His
            580                 585                 590

Asp Leu Tyr Val Ser Phe Asp Val Lys Asp Leu Gln Lys Ala Met Phe
        595                 600                 605

Arg Gln Gln Ser Phe Pro Ser Val Val Met Asn Pro Gln Asp Ala His
610                 615                 620

Ser Ala Tyr Ile Arg Gly Asp Val Glu Leu Val Arg Ile Arg Asp Ala
625                 630                 635                 640

Glu Gly Arg Ile Ala Ala Glu Gly Ala Leu Pro Tyr Pro Pro Gly Val
            645                 650                 655

Leu Cys Val Val Pro Gly Glu Val Trp Gly Gly Ala Val Gln Arg Tyr
            660                 665                 670

Phe Leu Ala Leu Glu Glu Gly Val Asn Leu Leu Pro Gly Phe Ser Pro
        675                 680                 685

Glu Leu Gln Gly Val Tyr Ser Glu Thr Asp Ala Asp Gly Val Lys Arg
    690                 695                 700

Leu Tyr Gly Tyr Val Leu Lys
705                 710
```

<210> SEQ ID NO 21
<211> LENGTH: 1407
<212> TYPE: DNA
<213> ORGANISM: Corynebacterium ammoniagenes DSM 20306

<400> SEQUENCE: 21

```
atgattggct tggataactc catcctcttt accgctcttc ccaccctgac cgaagagcta    60
cacgctggag aaacccaaca actgtggatt atcaacgcct atccctggt gcttgccggc    120 ttgttgctgg gcaccggaac cctaggggat aaaattggcc accgccgcat gttcaccacc    180
ggcctggtca ttttcggcgt cgcctcgctc gccgcagcgt tctccccaac tcccgcattt    240
```

```
ttgattggcg ctcgcgcggt cttgggcctt ggcgctgccg tgatgatgcc tgctactttg    300
gcgctcattc gcctaacctt cacaaatgag caagagcgca ataccgccat cggcatttgg    360
ggatcggtcg ccgtcgtcgg tgccgccgcg ggcccggtcg ttggcggcgc gctactggag    420
atgtggtggt ggggatctgt ctttctcatc aacgtcccca tcgtggtcat cgctttaatc    480
gccaccgcgt tgctggcccc accaaatatg cccaacccga ctaagcattg ggatttcagc    540
tcttctgtct atgcgctcat cgctctcgcg gggcttaccc tgaccatcaa ggaaatagcc    600
aaccccaacc gctcctgggt tctggtcgct gcggcgtttt tcgcctgcat cattggcgga    660
ttcctctttg ttcgccgtca gaataaattg gaagagcctc tgttgacctt cgatatcttc    720
cgtaatcgtc tcttcatcgg cggcgtgatt gctgcttcgg gcgcgatgtt tatcatggcc    780
ggactggaga tgatcacggc gcaaaagctt cagcttgccg atgatttcag ccccttccac    840
gccggcgtca tcgtcgccgt agcggcgatt gccgcactac cgacctccgc gctcggcggc    900
gccaacttgc accgcattgg ctttatcccg ctcatctctg gtggcttctt gctcagcacg    960
ctcggcaccg tgctggccat gtggtccgca cacgccgatt ccgtagccgt gttgattacc   1020
ggcttgatct tcttaggcgc cggcgcgggt gccacgatgt cggtgtcctc gattgcgatc   1080
atcggatctg ttccgatgca ccgttccggc atggccgccg cgtagaaga agtctcctac   1140 gaattcggca ccctttttgtc cgtagccttc gtcggatcgc tcaccccagc gctctacctg   1200
tctaacctgc ctgcgaacct caagcacatg gcaccgaag ctctgcacgg tggccttggt   1260
catgcggatg catcgaccgc gtatgcttct gcttacggca ccaccgtggg atgtgtagca   1320
gtatttgcat tcatcttcac gctggccacg ctctggtgct tccgaggaaa cccaaagtca   1380
ggaggaaacg gtggcgcgga cgagtaa                                       1407
```

<210> SEQ ID NO 22
<211> LENGTH: 497
<212> TYPE: PRT
<213> ORGANISM: Corynebacterium ammoniagenes DSM 20306

<400> SEQUENCE: 22

Met Arg Thr Ala Arg Lys Glu Phe His Asn Asn Ser Thr Pro Ala Gln
1               5                   10                  15

Arg Trp Ser Phe Phe Ala Ala Ile Ser Leu Gly Leu Leu Met Ile Gly
            20                  25                  30

Leu Asp Asn Ser Ile Leu Phe Thr Ala Leu Pro Thr Leu Thr Glu Glu
        35                  40                  45

Leu His Ala Gly Glu Thr Gln Gln Leu Trp Ile Ile Asn Ala Tyr Pro
    50                  55                  60

Leu Val Leu Ala Gly Leu Leu Gly Thr Gly Thr Leu Gly Asp Lys
65                  70                  75                  80

Ile Gly His Arg Arg Met Phe Thr Thr Gly Leu Val Ile Phe Gly Val
                85                  90                  95

Ala Ser Leu Ala Ala Phe Ser Pro Thr Pro Ala Phe Leu Ile Gly
            100                 105                 110

Ala Arg Ala Val Leu Gly Leu Gly Ala Ala Val Met Met Pro Ala Thr
        115                 120                 125

Leu Ala Leu Ile Arg Leu Thr Phe Thr Asn Glu Gln Glu Arg Asn Thr
    130                 135                 140

Ala Ile Gly Ile Trp Gly Ser Val Ala Val Gly Ala Ala Ala Gly
145                 150                 155                 160

Pro Val Val Gly Gly Ala Leu Leu Glu Met Trp Trp Trp Gly Ser Val

```
                    165                 170                 175
Phe Leu Ile Asn Val Pro Ile Val Ile Ala Leu Ile Ala Thr Ala
                180                 185                 190

Leu Leu Ala Pro Pro Asn Met Pro Asn Pro Thr Lys His Trp Asp Phe
            195                 200                 205

Ser Ser Ser Val Tyr Ala Leu Ile Ala Leu Ala Gly Leu Thr Leu Thr
            210                 215                 220

Ile Lys Glu Ile Ala Asn Pro Asn Arg Ser Trp Val Leu Val Ala Ala
225                 230                 235                 240

Ala Phe Phe Ala Cys Ile Ile Gly Gly Phe Leu Phe Val Arg Arg Gln
                245                 250                 255

Asn Lys Leu Glu Glu Pro Leu Leu Thr Phe Asp Ile Phe Arg Asn Arg
            260                 265                 270

Leu Phe Ile Gly Gly Val Ile Ala Ala Ser Gly Ala Met Phe Ile Met
            275                 280                 285

Ala Gly Leu Glu Met Ile Thr Ala Gln Lys Leu Gln Leu Ala Asp Asp
            290                 295                 300

Phe Ser Pro Phe His Ala Gly Val Ile Val Ala Val Ala Ile Ala
305                 310                 315                 320

Ala Leu Pro Thr Ser Ala Leu Gly Gly Ala Asn Leu His Arg Ile Gly
                325                 330                 335

Phe Ile Pro Leu Ile Ser Gly Gly Phe Leu Leu Ser Thr Leu Gly Thr
            340                 345                 350

Val Leu Ala Met Trp Ser Ala His Ala Asp Ser Val Ala Val Leu Ile
            355                 360                 365

Thr Gly Leu Ile Phe Leu Gly Ala Gly Ala Gly Ala Thr Met Ser Val
            370                 375                 380

Ser Ser Ile Ala Ile Ile Gly Ser Val Pro Met His Arg Ser Gly Met
385                 390                 395                 400

Ala Ala Gly Val Glu Glu Val Ser Tyr Glu Phe Gly Thr Leu Leu Ser
                405                 410                 415

Val Ala Phe Val Gly Ser Leu Thr Pro Ala Leu Tyr Leu Ser Asn Leu
            420                 425                 430

Pro Ala Asn Leu Lys His Met Gly Thr Glu Ala Leu His Gly Gly Leu
            435                 440                 445

Gly His Ala Asp Ala Ser Thr Ala Tyr Ala Ser Ala Tyr Gly Thr Thr
            450                 455                 460

Val Gly Cys Val Ala Val Phe Ala Phe Ile Phe Thr Leu Ala Thr Leu
465                 470                 475                 480

Trp Cys Phe Arg Gly Asn Pro Lys Ser Gly Gly Asn Gly Gly Ala Asp
                485                 490                 495

Glu

<210> SEQ ID NO 23
<211> LENGTH: 1362
<212> TYPE: DNA
<213> ORGANISM: Corynebacterium lipophiloflavum DSM 44291

<400> SEQUENCE: 23
atgcgttggt tgcttctcgg cgtcctctcc accggccttc tgctcatcgg gctggacaac     60
tcgatcctgt acacggcact gcccaccatc agcgccgagc tgggtgcgga cgaggcacag    120
ggcctgtgga tcatcaacgc ctacccgctc gtagtggctg gtctgatgct ggacaccggc    180
accctcggtg acaaggtggg ccacgcgcgc atgttcgcca cgggcatggc catcttcggt    240
```

```
gcagcctccc tgagctgcgc ctacgctccc acgccagagc tgctcatcgc cgcgcgcggc    300
gcactcggcc tcggcgcggc tgtgatgatg ccggccacgc tcgcgctcgt gcagcagacg    360
tttccaaacg agcgcgagcg caacacggcg atcggcatct gggcctccgt agctaccgcg    420
ggtgccgcgg ccgccccgct cgtcggcggg ttcttgctgg agcatttctg gtggggctcg    480
atcttcctcg tcaacgtgcc atcgtcgcg gccgccctgc tcgctctcgc cgcgctgcgc    540
cccaccaatc accccctaccc tctggtgcgc tgggacgcgg cctcgacact gctgagcatc    600
ctcaccctca ccgggttcac gctggtcatc aaaggacacc tgtgggccgt cgtgccggcg    660
gggctcggcg cgtggttgtt tgcgcgtcga caagcgcggc tcgagcaacc gttgctcacg    720
ctcgacatct tccgcaaccg catcttcagc ggcggtgtcg tcgccgctgc gctcgcgctg    780
accgggctcg ccgccgtaga gctgctgacc acccagcgtt tccacatcgt cgccgggttc    840
agcccgctcg aggcgggcgc gatcatctcg gcgatcgtcg cggcgtcgct gccgtcgtcg    900
atcatcggcg ggatggtgct ccaccgcgtc gggttcttcc cgctcatcgt gggcgggctg    960
accacggcgg ccaccggcac cctcgtggct gcgctggccg tgcacaccct cccggtcttc   1020
atcacggcga tgctgttcgt gggcgccggc atcggggccg tcggcagcgt cgcctccacc   1080
gcaatcgtcg gctcggcacc accccaccgc gaaggcatgg cggcgagcgt ggaggaaatc   1140
tcctacgagc tcggggcgct caccggagtg gccctgctcg aacgctgat gagcaccatc   1200 ctcgcgcgtt tcgacgactc cacaacgcac ccgcacgcgg tttacgacat ggcctactca   1260
accgtgctca ccatcgccgc ggcgatccta ctggccagcg cgttcgcctg cgcctggctg   1320
tttcgcggca acccgaaacg ccctgcccac cagcgcagtt ag                      1362
```

<210> SEQ ID NO 24
<211> LENGTH: 457
<212> TYPE: PRT
<213> ORGANISM: Corynebacterium lipophiloflavum DSM 44291

<400> SEQUENCE: 24

```
Met Leu Arg Ala Met Arg Trp Leu Leu Leu Gly Val Leu Ser Thr Gly
1               5                   10                  15

Leu Leu Leu Ile Gly Leu Asp Asn Ser Ile Leu Tyr Thr Ala Leu Pro
            20                  25                  30

Thr Ile Ser Ala Glu Leu Gly Ala Asp Glu Ala Gln Gly Leu Trp Ile
        35                  40                  45

Ile Asn Ala Tyr Pro Leu Val Val Ala Gly Leu Met Leu Gly Thr Gly
    50                  55                  60

Thr Leu Gly Asp Lys Val Gly His Ala Arg Met Phe Ala Thr Gly Met
65                  70                  75                  80

Ala Ile Phe Gly Ala Ala Ser Leu Ser Cys Ala Tyr Ala Pro Thr Pro
                85                  90                  95

Glu Leu Leu Ile Ala Ala Arg Gly Ala Leu Gly Leu Gly Ala Ala Val
            100                 105                 110

Met Met Pro Ala Thr Leu Ala Leu Val Gln Gln Thr Phe Pro Asn Glu
        115                 120                 125

Arg Glu Arg Asn Thr Ala Ile Gly Ile Trp Ala Ser Val Ala Thr Ala
    130                 135                 140

Gly Ala Ala Ala Gly Pro Leu Val Gly Gly Phe Leu Leu Glu His Phe
145                 150                 155                 160

Trp Trp Gly Ser Ile Phe Leu Val Asn Val Pro Ile Val Ala Ala Ala
                165                 170                 175
```

Leu Leu Ala Leu Ala Ala Leu Arg Pro Thr Asn His Pro Tyr Pro Leu
            180                 185                 190

Val Arg Trp Asp Ala Ala Ser Thr Leu Leu Ser Ile Leu Thr Leu Thr
        195                 200                 205

Gly Phe Thr Leu Val Ile Lys Gly His Leu Trp Ala Val Val Pro Ala
    210                 215                 220

Gly Leu Gly Ala Trp Leu Phe Ala Arg Arg Gln Ala Arg Leu Glu Gln
225                 230                 235                 240

Pro Leu Thr Leu Asp Ile Phe Arg Asn Arg Ile Phe Ser Gly Gly
            245                 250                 255

Val Val Ala Ala Ala Leu Ala Leu Thr Gly Leu Ala Ala Val Glu Leu
            260                 265                 270

Leu Thr Thr Gln Arg Phe His Ile Val Ala Gly Phe Ser Pro Leu Glu
            275                 280                 285

Ala Gly Ala Ile Ile Ser Ala Ile Val Ala Ala Ser Leu Pro Ser Ser
            290                 295                 300

Ile Ile Gly Gly Met Val Leu His Arg Val Gly Phe Phe Pro Leu Ile
305                 310                 315                 320

Val Gly Gly Leu Thr Thr Ala Ala Thr Gly Thr Leu Val Ala Ala Leu
            325                 330                 335

Ala Val His Thr Leu Pro Val Phe Ile Thr Ala Met Leu Phe Val Gly
            340                 345                 350

Ala Gly Ile Gly Ala Val Gly Ser Val Ala Ser Thr Ala Ile Val Gly
            355                 360                 365

Ser Ala Pro Pro His Arg Glu Gly Met Ala Ala Ser Val Glu Glu Ile
            370                 375                 380

Ser Tyr Glu Leu Gly Ala Leu Thr Gly Val Ala Leu Leu Gly Thr Leu
385                 390                 395                 400

Met Ser Thr Ile Leu Ala Arg Phe Asp Asp Ser Thr Thr His Pro His
            405                 410                 415

Ala Val Tyr Asp Met Ala Tyr Ser Thr Val Leu Thr Ile Ala Ala Ala
            420                 425                 430

Ile Leu Leu Ala Ser Ala Phe Ala Cys Ala Trp Leu Phe Arg Gly Asn
            435                 440                 445

Pro Lys Arg Pro Ala His Gln Arg Ser
    450                 455

<210> SEQ ID NO 25
<211> LENGTH: 2142
<212> TYPE: DNA
<213> ORGANISM: Escherichia coli

<400> SEQUENCE: 25
atgaacatca ttgccattat gggaccgcat ggcgtctttt ataaagatga gcccatcaaa     60
gaactggagt cggcgctggt ggcgcaaggc tttcagatta tctggccaca aaacagcgtt    120
gatttgctga aatttatcga gcataaccct cgaatttgcg gcgtgatttt tgactgggat    180
gagtacagtc tcgatttatg tagcgatatc aatcagctta atgaatatct cccgcttat    240 gccttcatca cacccactc gacgatggat gtcagcgtgc aggatatgcg gatggcgctc    300
tggttttttg aatatgcgct ggggcaggcg aagatatcg ccattcgtat gcgtcagtac    360
accgacgaat atcttgataa cattacaccg ccgttcacga aagccttgtt tacctacgtc    420
aaagagcgga agtacaccct ttgtacgccg gggcatatgg gcggcaccgc atatcaaaaa    480

-continued

```
agcccggttg gctgtctgtt ttatgattt ttcggcggga atactcttaa ggctgatgtc    540
tctatttcgg tcaccgagct tggttcgttg ctcgaccaca ccgggccaca cctggaagcg    600
gaagagtaca tcgcgcggac ttttggcgcg aacagagtt atatcgttac caacggaaca    660
tcgacgtcga acaaaattgt gggtatgtac gccgcgccat ccggcagtac gctgttgatc    720
gaccgcaatt gtcataaatc gctggcgcat ctgttgatga tgaacgatgt agtgccagtc    780
tggctgaaac cgacgcgtaa tgcgttgggg attcttggtg ggatcccgcg ccgtgaattt    840
actcgcgaca gcatcgaaga gaaagtcgct gctaccacgc aagcacaatg gccggttcat    900
gcggtgatca ccaactccac ctatgatggc ttgctctaca caccgactg gatcaaacag     960 acgctggatg tcccgtcgat tcacttcgat tctgcctggg tgccgtacac ccattttcat   1020
ccgatctacc agggtaaaag tggtatgagc ggcgagcgtg ttgcgggaaa agtgatcttc   1080
gaaacgcaat cgacccacaa aatgctggcg gcgttatcgc aggcttcgct gatccacatt   1140
aaaggcgagt atgacgaaga ggcctttaac gaagccttta tgatgcatac caccacctcg   1200
cccagttatc ccattgttgc ttcggttgag acggcggcgg cgatgctgcg tggtaatccg   1260
ggcaaacggc tgattaaccg ttcagtagaa cgagctctgc attttcgcaa agaggtccag   1320
cggctgcggg aagagtctga cggttggttt ttcgatatct ggcaaccgcc gcaggtggat   1380
gaagccgaat gctggcccgt tgcgcctggc aacagtggc acggctttaa cgatgcggat   1440
gccgatcata tgtttctcga tccggttaaa gtcactattt tgacaccggg gatggacgag   1500
cagggcaata tgagcgagga ggggatcccg gcggcgctgg tagcaaaatt cctcgacgaa   1560
cgtgggatcg tagtagagaa aaccggcccct tataacctgc tgtttctctt tagtattggc   1620
atcgataaaa ccaaagcaat gggattattg cgtgggttga cggaattcaa acgctcttac   1680
gatctcaacc tgcggatcaa aaatatgcta cccgatctct atgcagaaga tcccgatttc   1740
taccgcaata tgcgtattca ggatctggca caagggatcc ataagctgat tcgtaaacac   1800
gatcttcccg gtttgatgtt gcgggcattc gatactttgc cggagatgat catgacgcca   1860
catcaggcat ggcaacgaca aattaaaggc gaagtagaaa ccattgcgct ggaacaactg   1920
gtcggtagag tatcggcaaa tatgatcctg ccttatccac cgggcgtacc gctgttgatg   1980
cctggagaaa tgctgaccaa agagagccgc acagtactcg attttctact gatgctttgt   2040
tccgtcgggc aacattaccc cggttttgaa acggatattc acggcgcgaa acaggacgaa   2100
gacggcgttt accgcgtacg agtcctaaaa atggcgggat aa                      2142
```

<210> SEQ ID NO 26
<211> LENGTH: 713
<212> TYPE: PRT
<213> ORGANISM: Escherichia coli

<400> SEQUENCE: 26

```
Met Asn Ile Ile Ala Ile Met Gly Pro His Gly Val Phe Tyr Lys Asp
1               5                   10                  15

Glu Pro Ile Lys Glu Leu Glu Ser Ala Leu Val Ala Gln Gly Phe Gln
                20                  25                  30

Ile Ile Trp Pro Gln Asn Ser Val Asp Leu Leu Lys Phe Ile Glu His
            35                  40                  45

Asn Pro Arg Ile Cys Gly Val Ile Phe Asp Trp Asp Glu Tyr Ser Leu
        50                  55                  60

Asp Leu Cys Ser Asp Ile Asn Gln Leu Asn Glu Tyr Leu Pro Leu Tyr
65                  70                  75                  80
```

-continued

```
Ala Phe Ile Asn Thr His Ser Thr Met Asp Val Ser Val Gln Asp Met
                 85                  90                  95
Arg Met Ala Leu Trp Phe Phe Glu Tyr Ala Leu Gly Gln Ala Glu Asp
            100                 105                 110
Ile Ala Ile Arg Met Arg Gln Tyr Thr Asp Glu Tyr Leu Asp Asn Ile
        115                 120                 125
Thr Pro Pro Phe Thr Lys Ala Leu Phe Thr Tyr Val Lys Glu Arg Lys
    130                 135                 140
Tyr Thr Phe Cys Thr Pro Gly His Met Gly Gly Thr Ala Tyr Gln Lys
145                 150                 155                 160
Ser Pro Val Gly Cys Leu Phe Tyr Asp Phe Phe Gly Asn Thr Leu
                165                 170                 175
Lys Ala Asp Val Ser Ile Ser Val Thr Glu Leu Gly Ser Leu Leu Asp
            180                 185                 190
His Thr Gly Pro His Leu Glu Ala Glu Glu Tyr Ile Ala Arg Thr Phe
        195                 200                 205
Gly Ala Glu Gln Ser Tyr Ile Val Thr Asn Gly Thr Ser Thr Ser Asn
    210                 215                 220
Lys Ile Val Gly Met Tyr Ala Ala Pro Ser Gly Ser Thr Leu Leu Ile
225                 230                 235                 240
Asp Arg Asn Cys His Lys Ser Leu Ala His Leu Leu Met Met Asn Asp
                245                 250                 255
Val Val Pro Val Trp Leu Lys Pro Thr Arg Asn Ala Leu Gly Ile Leu
            260                 265                 270
Gly Gly Ile Pro Arg Arg Glu Phe Thr Arg Asp Ser Ile Glu Glu Lys
        275                 280                 285
Val Ala Ala Thr Thr Gln Ala Gln Trp Pro Val His Ala Val Ile Thr
    290                 295                 300
Asn Ser Thr Tyr Asp Gly Leu Leu Tyr Asn Thr Asp Trp Ile Lys Gln
305                 310                 315                 320
Thr Leu Asp Val Pro Ser Ile His Phe Asp Ser Ala Trp Val Pro Tyr
                325                 330                 335
Thr His Phe His Pro Ile Tyr Gln Gly Lys Ser Gly Met Ser Gly Glu
            340                 345                 350
Arg Val Ala Gly Lys Val Ile Phe Glu Thr Gln Ser Thr His Lys Met
        355                 360                 365
Leu Ala Ala Leu Ser Gln Ala Ser Leu Ile His Ile Lys Gly Glu Tyr
    370                 375                 380
Asp Glu Glu Ala Phe Asn Glu Ala Phe Met Met His Thr Thr Thr Ser
385                 390                 395                 400
Pro Ser Tyr Pro Ile Val Ala Ser Val Glu Thr Ala Ala Ala Met Leu
                405                 410                 415
Arg Gly Asn Pro Gly Lys Arg Leu Ile Asn Arg Ser Val Glu Arg Ala
            420                 425                 430
Leu His Phe Arg Lys Glu Val Gln Arg Leu Arg Glu Glu Ser Asp Gly
        435                 440                 445
Trp Phe Phe Asp Ile Trp Gln Pro Pro Gln Val Asp Glu Ala Glu Cys
    450                 455                 460
Trp Pro Val Ala Pro Gly Glu Gln Trp His Gly Phe Asn Asp Ala Asp
465                 470                 475                 480
Ala Asp His Met Phe Leu Asp Pro Val Lys Val Thr Ile Leu Thr Pro
                485                 490                 495
Gly Met Asp Glu Gln Gly Asn Met Ser Glu Glu Gly Ile Pro Ala Ala
```

```
                500             505             510
Leu Val Ala Lys Phe Leu Asp Glu Arg Gly Ile Val Val Glu Lys Thr
            515                 520                 525
Gly Pro Tyr Asn Leu Leu Phe Leu Phe Ser Ile Gly Ile Asp Lys Thr
        530                 535                 540
Lys Ala Met Gly Leu Leu Arg Gly Leu Thr Glu Phe Lys Arg Ser Tyr
545                 550                 555                 560
Asp Leu Asn Leu Arg Ile Lys Asn Met Leu Pro Asp Leu Tyr Ala Glu
                565                 570                 575
Asp Pro Asp Phe Tyr Arg Asn Met Arg Ile Gln Asp Leu Ala Gln Gly
            580                 585                 590
Ile His Lys Leu Ile Arg Lys His Asp Leu Pro Gly Leu Met Leu Arg
        595                 600                 605
Ala Phe Asp Thr Leu Pro Glu Met Ile Met Thr Pro His Gln Ala Trp
        610                 615                 620
Gln Arg Gln Ile Lys Gly Glu Val Gly Thr Ile Ala Leu Glu Gln Leu
625                 630                 635                 640
Val Gly Arg Val Ser Ala Asn Met Ile Leu Pro Tyr Pro Pro Gly Val
                645                 650                 655
Pro Leu Leu Met Pro Gly Glu Met Leu Thr Lys Glu Ser Arg Thr Val
            660                 665                 670
Leu Asp Phe Leu Leu Met Leu Cys Ser Val Gly Gln His Tyr Pro Gly
        675                 680                 685
Phe Glu Thr Asp Ile His Gly Ala Lys Gln Asp Glu Asp Gly Val Tyr
        690                 695                 700
Arg Val Arg Val Leu Lys Met Ala Gly
705                 710
```

```
<210> SEQ ID NO 27
<211> LENGTH: 33
<212> TYPE: DNA
<213> ORGANISM: Artificial Sequence
<220> FEATURE:
<223> OTHER INFORMATION: CJ7-F_KpnI Primer

<400> SEQUENCE: 27
cggggtacca gaaacatccc agcgctacta ata                              33

<210> SEQ ID NO 28
<211> LENGTH: 32
<212> TYPE: DNA
<213> ORGANISM: Artificial Sequence
<220> FEATURE:
<223> OTHER INFORMATION: CJ7-R-HindIII Primer

<400> SEQUENCE: 28
cccaagctta gtgtttcctt tcgttgggta cg                               32

<210> SEQ ID NO 29
<211> LENGTH: 38
<212> TYPE: DNA
<213> ORGANISM: Artificial Sequence
<220> FEATURE:
<223> OTHER INFORMATION: ldcC-F_HindIII Primer

<400> SEQUENCE: 29
cccaagctta agcttatgaa catcattgcc attatggg                         38

<210> SEQ ID NO 30
```

```
<211> LENGTH: 32
<212> TYPE: DNA
<213> ORGANISM: Artificial Sequence
<220> FEATURE:
<223> OTHER INFORMATION: ldcC-R_XbaI Primer

<400> SEQUENCE: 30
tgctctagat tatcccgcca tttttaggac tc                                    32

<210> SEQ ID NO 31
<211> LENGTH: 41
<212> TYPE: DNA
<213> ORGANISM: Artificial Sequence
<220> FEATURE:
<223> OTHER INFORMATION: HMPREF0281_01446-Forward Primer

<400> SEQUENCE: 31
caacgaaagg aaacactatg attggcttgg ataactccat c                          41

<210> SEQ ID NO 32
<211> LENGTH: 34
<212> TYPE: DNA
<213> ORGANISM: Artificial Sequence
<220> FEATURE:
<223> OTHER INFORMATION: HMPREF0281_01446-Reverse Primer

<400> SEQUENCE: 32
gaatgagttc ctcgagttac tcgtccgcgc cacc                                  34

<210> SEQ ID NO 33
<211> LENGTH: 37
<212> TYPE: DNA
<213> ORGANISM: Artificial Sequence
<220> FEATURE:
<223> OTHER INFORMATION: HMPREF0298_0262-Forward Primer

<400> SEQUENCE: 33
caacgaaagg aaacactatg cgttggttgc ttctcgg                               37

<210> SEQ ID NO 34
<211> LENGTH: 34
<212> TYPE: DNA
<213> ORGANISM: Artificial Sequence
<220> FEATURE:
<223> OTHER INFORMATION: HMPREF0298_0262-Reverse Primer

<400> SEQUENCE: 34
gaatgagttc ctcgagctaa ctgcgctggt gggc                                  34
```

MICROORGANISMS FOR PRODUCING DIAMINE AND PROCESS FOR PRODUCING DIAMINE USING THEM

CROSS-REFERENCES TO RELATED APPLICATIONS

This application is a U.S. national phase application of International PCT Patent Application No. PCT/KR2015/003065, which was filed on Mar. 27, 2015, which claims priority to Korean Patent Application Nos. 10-2014-0049870, filed Apr. 25, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_050_00US_ST25.txt. The text file is 62 KB, was created on Oct. 25, 2016, and is being submitted electronically via EFS-Web.

TECHNICAL FIELD

The present disclosure relates to a microorganism for producing diamine and a method of producing diamine using the same.

BACKGROUND ART

Biogenic amines (BAs) are nitrogenous compounds which are mainly produced by decarboxylation of amino acids or by amination and transamination of aldehydes and ketones. These biogenic amines are low molecular weight compounds and synthesized in the metabolism of microorganisms, plants and animals, and thus biogenic amines are known as components frequently found in these cells. In particular, biogenic amines are polyamines such as spermidine, spermine, putrescine or 1,4-butanediamine, and cadaverine.

In general, putrescine is an important raw material for production of polyamine nylon-4,6 which is produced by reacting putrescine with adipic acid. Putrescine is usually produced by chemical synthesis involving conversion of propylene to acrylonitrile and to succinonitrile.

As a production method of putrescine using a microorganism, a method of producing putrescine at a high concentration by transformation of *E. coli* and *Corynebacterium* has been reported (International Patent Publication No. WO06/005603; International Patent Publication No. WO09/125924; Qian Z D et al., Biotechnol. Bioeng. 104: 4, 651-662, 2009; Schneider et al., Appl. Microbiol, Biotechnol. 88; 4, 859-868, 2010; Schneider et al., Appl. Microbiol. Biotechnol. 95, 169-178, 2012). Furthermore, studies have been actively conducted on putrescine transporters in *E. coli*, yeast, plant and animal cells (K Igarashi, Plant Physiol. Biochem. 48: 506-512, 2010).

Meanwhile, cadaverine is a foul-smelling diamine compound produced by protein hydrolysis during putrefaction of animal tissues. Cadaverine has the chemical formula of $NH_2(CH_2)_5NH_2$, which is similar to that of putrescine.

Cadaverine serves as a component of polymers such as polyamide or polyurethane, chelating agents, or other additives. In particular, polyamide having an annual global market of 3.5 million tons is known to be prepared by polycondensation of cadaverine or succinic acid, and thus cadaverine has received much attention as an industrially useful compound.

Cadaverine is a diamine found in a few microorganisms (Tabor and Tabor, Microbiol Rev., 49:81-99, 1985). In the gram negative bacterium *E. coli*, cadaverine is biosynthesized from L-lysine by L-lysine decarboxylase. The level of cadaverine in *E. coli* is regulated by biosynthesis, degradation, uptake and export of cadaverine (Soksawatmaekhin et al., Mol Microbiol., 51:1401-1412, 2004).

DISCLOSURE

Technical Problem

The present inventors have made intensive efforts to investigate a protein having an ability to export diamine such as putrescine or cadaverine so as to improve diamine productivity in a microorganism having the diamine productivity. As a result, they found that a *Corynebacterium efficiens*-derived protein or a protein having high amino acid sequence homology therewith has a diamine export activity, and this protein is introduced into a microorganism for producing diamine to enhance its activity, resulting in a remarkable increase in the ability to export diamine such as putrescine and cadaverine, thereby completing the present invention.

Technical Solution

An object of the present invention is to provide a microorganism for producing diamine.

Another object of the present invention is to provide a method of producing diamine, including the steps of (i) culturing the microorganism for producing diamine to obtain a cell culture; and (ii) recovering diamine from the cultured microorganism or the cell culture.

BEST MODE

In an aspect to achieve the above objects, the present invention provides a microorganism for producing diamine, in which activity of a protein having an amino acid sequence of SEQ ID NO: 6 or an amino acid sequence having 55% or higher sequence homology with SEQ ID NO:6 is introduced or enhanced.

As used herein, the term "diamine" collectively refers to a compound having two amine groups, and specific examples thereof may include putrescine and cadaverine. Putrescine is tetramethylenediamine which may be produced from ornithine as a precursor. Cadaverine is called 1,5-pentanediamine or pentamethylenediamine, which may be produced from lysine as a precursor. Such diamines are industrially applicable compounds that serve as valuable raw materials for synthesis of polymers such as polyamine nylon, polyamide or polyurethane.

As used herein, the term "protein having an amino acid sequence of SEQ ID NO: 6" is a protein found in *Corynebacterium efficiens*, and also called CE2495. It was investigated that this protein retains high homology with a membrane protein of *Corynebacterium*, NCgl2522. In an embodiment of the present invention, CE2495 protein is identified as a putative protein which is involved in diamine export in a strain having diamine productivity, thereby remarkably increasing diamine productivity.

Here, CE2495 protein having the amino acid sequence of SEQ ID NO: 6 may be a protein that is encoded by a nucleotide sequence of SEQ ID NO: 5. In the polynucleotide encoding the CE2495 protein, however, various modifications may be made in the coding region provided that they do not change the amino acid sequence of the polypeptide expressed from the coding region, due to codon degeneracy or in consideration of the codons preferred by an organism in which the protein is to be expressed. Thus, the CE2495 protein may be encoded by various nucleotide sequences as well as by the nucleotide sequence of SEQ ID NO: 5.

Further, the CE2495 protein of the present invention may be any protein having the amino acid sequence of SEQ ID NO: 6, or having 55% or higher, preferably 75% or higher, more preferably 90% or higher, much more preferably 95% or higher, even much more preferably 98% or higher, and most preferably 99% or higher homology therewith, as long as the protein exhibits a substantial diamine export activity. It is apparent that an amino acid sequence having such homology, of which a part is deleted, modified, substituted, or added, is also within the scope of the present invention, as long as the resulting amino acid sequence has a biological activity substantially equivalent or corresponding to the protein of SEQ ID NO: 6.

As used herein, the term "protein having an amino acid sequence having 55% or higher sequence homology with the amino acid sequence of SEQ ID NO: 6" means any protein without limitation, as long as the protein has an amino acid sequence having 55% or higher sequence homology with the amino acid sequence of SEQ ID NO: 6 and it also has substantially diamine export activity. For example, the protein may be a protein having an amino acid sequence of SEQ ID NO: 22 or SEQ ID NO: 24, but is not limited thereto.

For example, the protein having the amino acid sequence of SEQ ID NO: 22 is a protein found in *Corynebacterium ammoniagenes*, and also called HMPREF0281_01446. It was investigated that this protein retains 59% homology with a membrane protein of *Corynebacterium*, NCgl2522 and 61% homology with CE2495 of *Corynebacterium efficiens*. In an embodiment of the present invention, it was investigated that the HMPREF0281_01446 protein exhibits diamine export activity in a strain having diamine productivity, thereby remarkably increasing diamine productivity.

The HMPREF0281_01446 protein having the amino acid sequence of SEQ ID NO. 22 may be a protein that is encoded by a nucleotide sequence of SEQ ID NO: 21. In the polynucleotide encoding this protein, however, various modifications may be made in the coding region provided that they do not change the amino acid sequence of the polypeptide expressed from the coding region, due to codon degeneracy or in consideration of the codons preferred by an organism in which the protein is to be expressed. Thus, this protein may be encoded by various nucleotide sequences as well as by the nucleotide sequence of SEQ ID NO: 21.

Further, the protein having the amino acid sequence of SEQ ID NO: 24 is a protein found in *Corynebacterium lipophiloflavum*, and also called HMPREF0298_0262. It was investigated that this protein retains 52% homology with a membrane protein of *Corynebacterium*, NCgl2522 and 56% homology with CE2495 of *Corynebacterium efficiens*. In an embodiment of the present invention, it was investigated that the HMPREF0298_0262 protein exhibits diamine export activity in a strain having diamine productivity, thereby remarkably increasing diamine productivity.

The HMPREF0298_0262 protein having the amino acid a nucleotide sequence of SEQ ID NO: 23. In the polynucleotide encoding this protein, however, various modifications may be made in the coding region provided that they do not change the amino acid sequence of the polypeptide expressed from the coding region, due to codon degeneracy or in consideration of the codons preferred by an organism in which the protein is to be expressed. Thus, this protein may be encoded by various nucleotide sequences as well as by the nucleotide sequence of SEQ ID NO: 23.

The term "homology", as used herein with regard to a sequence, refers to identity with a given amino acid sequence or nucleotide sequence, and the homology may be expressed as a percentage. In the present invention, a homology sequence having identical or similar activity to the given amino acid sequence or nucleotide sequence is expressed as "% homology". For example, homology may be identified using a standard software program which calculates parameters of score, identity and similarity, specifically BLAST 2.0, or by comparing sequences in a Southern hybridization experiment under stringent conditions as defined. Defining appropriate hybridization conditions are within the skill of the art (e.g., see Sambrook et al., 1989, infra), and determined by a method known to those skilled in the art.

As used herein, the term "microorganism for producing diamine" refers to a microorganism prepared by providing diamine productivity for a parent strain having no diamine productivity or a microorganism having endogenous diamine productivity. Specifically, the microorganism having diamine productivity may be a microorganism having putrescine or cadaverine productivity.

The "microorganism having putrescine productivity" may be, but is not limited to, a microorganism in which the activity of acetylglutamate synthase that converts glutamate to N-acetylglutamate, ornithine acetyltransferase (ArgJ) that converts acetyl ornithine to ornithine, acetylglutamate kinase (ArgB) that converts acetyl glutamate to N-acetylglutamyl phosphate, acetyl-gamma-glutamyl-phosphate reductase (ArgC) that converts acetyl glutamyl phosphate to N-acetyl glutamate semialdehyde, or acetylornithine aminotransferase (ArgD) that converts acetyl glutamate semialdehyde to N-acetylornithine is enhanced compared to its endogenous activity, in order to enhance the biosynthetic pathway from glutamate to ornithine, and the productivity of ornithine which is used as a precursor for putrescine biosynthesis is enhanced, but is not limited thereto.

Further, the microorganism having putrescine productivity may be a microorganism which is modified to have activity of ornithine carbamoyl transferase (ArgF) involved in synthesis of arginine from ornithine, a protein (NCgl1221) involved in glutamate export, and/or a protein (NCgl469) involved in putrescine acetylation weaker than its endogenous activity, and/or is modified to be introduced with activity of ornithine decarboxylase (ODC).

Here, as non-limiting examples, the acetyl gamma glutamyl phosphate reductase (ArgC) may have an amino acid sequence of SEQ ID NO: 14, the acetylglutamate synthase or ornithine acetyltransferase (ArgJ) may have an amino acid sequence of SEQ ID NO: 15, the acetyl glutamate kinase (ArgB) may have an amino acid sequence of SEQ ID NO: 16, and the acetylornithine aminotransferase (ArgD) may have an amino acid sequence of SEQ ID NO: 14. However, the amino acid sequences of respective enzyme proteins are not particularly limited thereto, and the enzymes may be proteins having amino acid sequences having 80% or higher, preferably 90% or higher, or more preferably 95% or higher homology therewith, as long as they have activities of the respective enzymes.

Further, as non-limiting examples, the ornithine carbamoyl transferase (ArgF) may have an amino acid sequence of SEQ ID NO: 18, the protein involved in glutamate export may have an amino acid sequence of SEQ ID NO: 19, and ornithine decarboxylase (ODC) may have an amino acid sequence of SEQ ID NO: 20. However, the amino acid sequences of respective enzyme proteins are not limited thereto, and the enzymes may be proteins having amino acid sequences having 80% or higher, preferably 90% or higher, more preferably 95% or higher, or particularly preferably 97% or higher homology therewith, as long as they have activities of the respective enzymes.

Meanwhile, the "microorganism having cadaverine productivity" may be, but is not limited to, a microorganism prepared by additionally introducing or enhancing activity of lysine decarboxylase (LDC) in a microorganism having lysine productivity. For example, the microorganism may be one having enhanced lysine productivity in order to increase cadaverine production. A method of enhancing lysine productivity may be performed by a known method which is predictable to those skilled in the art.

The lysine decarboxylase is an enzyme catalyzing conversion of lysine to cadaverine, and its activity is introduced or enhanced, thereby effectively producing cadaverine.

The lysine decarboxylase may have an amino acid sequence of SEQ ID NO: 26, but is not particularly limited thereto. The enzyme may have an amino acid sequence having 80% or higher, preferably 90% or higher, or more preferably 95% or higher homology therewith, as long as it has the above activity.

As used herein, the term "production" is a concept including extracellular release of diamine, for example, release of diamine into a culture medium, as well as production of diamine within a microorganism.

Meanwhile, the term "introduction of protein activity", as used herein, means that a microorganism having no endogenous protein is externally provided with an activity of the protein, and for example, it may be performed by introduction of a foreign gene. Further, the term "enhancement of protein activity" means that active state of the protein retained in or introduced into the microorganism is enhanced, compared to its intrinsic active state.

Non-limiting examples of the introduction or enhancement of the protein activity may include improvement of the activity of the protein itself present in a microorganism due to mutation so as to achieve effects beyond the endogenous functions, and/or improvement in endogenous gene activity of the protein present in the microorganism, amplification of the endogenous gene by internal or external factors, increase in the gene copy number, increase in the activity by additional introduction of a foreign gene or replacement or modification of a promoter, but are not limited thereto.

The increase in the gene copy number may be, but is not particularly limited to, performed by operably linking the gene to a vector or by integrating it into the host cell genome. Specifically, the copy number of the polynucleotide in the host cell genome may be increased by introducing into the host cell the vector which is operably linked to the polynucleotide encoding the protein of the present invention and replicates and functions independently of the host cell, or by introducing into the host cell the vector which is operably linked to the polynucleotide and is able to integrate the polynucleotide into the host cell genome.

As used herein, "modification of the expression regulatory sequence for increasing the polynucleotide expression" may be, but is not particularly limited to, done by inducing a modification on the expression regulatory sequence through deletion, insertion, non-conservative or conservative substitution of nucleotide sequence, or a combination thereof in order to further enhance the activity of expression regulatory sequence, or by replacing the expression regulatory sequence with a nucleotide sequence having stronger activity. The expression regulatory sequence includes, but is not particularly limited to, a promoter, an operator sequence, a sequence coding for a ribosome-binding site, and a sequence regulating the termination of transcription and translation.

As used herein, the replacement or modification of a promoter, although not particularly limited thereto, may be performed by replacement or modification with a stronger promoter than the original promoter. A strong heterologous promoter instead of the original promoter may be linked upstream of the polynucleotide expression unit, and examples of the strong promoter may include a CJ7 promoter, a lysCP1 promoter, an EF-Tu promoter, a groEL promoter, an aceA or aceB promoter, and specifically, a *Corynebacterium*-derived promoter, lysCP1 promoter or CJ7 promoter is operably linked to the polynucleotide encoding the enzyme so that its expression rate may be increased. Here, the lysCP1 promoter is a promoter improved through nucleotide sequence substitution of the promoter region of the polynucleotide encoding aspartate kinase and aspartate semialdehyde dehydrogenase (WO 2009/096689). Further, CJ7 promoter is a strong promoter derived from *Corynebacterium* ammoniagenes (Korean Patent No. 0620092 and WO 2006/065095).

Furthermore, modification of a polynucleotide sequence on chromosome, although not particularly limited thereto, may be performed by inducing a mutation on the expression regulatory sequence through deletion, insertion, non-conservative or conservative substitution of polynucleotide sequence, or a combination thereof in order to further enhance the activity of the polynucleotide sequence, or by replacing the sequence with a polynucleotide sequence which is modified to have stronger activity.

As used herein, the term "vector" refers to a DNA construct including a nucleotide sequence encoding the desired protein, which is operably linked to an appropriate expression regulatory sequence to express the desired protein in a suitable host cell. The regulatory sequence may include a promoter that can initiate transcription, an optional operator sequence for regulating the transcription, a sequence encoding a suitable mRNA ribosome binding site, and a sequence regulating the termination of transcription and translation. After the vector is introduced into the suitable host cell, it may replicate or function independently of the host genome, and may be integrated into the genome itself.

The vector used in the present invention is not particularly limited, as long as it is able to replicate in the host cell, and any vector known in the art may be used. Examples of conventional vectors may include a natural or recombinant plasmid, cosmid, virus and bacteriophage. For instance, pWE15, M13, λMBL3, λMBL4, λIXII, λASHII, λAPII, λt10, λt11, Charon4A, and Charon21A may be used as a phage vector or cosmid vector. pBR type, pUC type, pBluescriptII type, pGEM type, pTZ type, pCL type and pET type may be used as a plasmid vector. A vector usable in the present invention is not particularly limited, and any known expression vector may be used. Preferably, pDZ, pACYC177, pACYC184, pCL, pECCG117, pUC19, pBR322, pMW118, or pCC1BAC vector may be used.

Further, the polynucleotide encoding the desired endogenous protein in the chromosome can be replaced by a mutated polynucleotide using a vector for bacterial chromosomal insertion. The insertion of the polynucleotide into the chromosome may be performed by any method known in the art, for example, homologous recombination. Since the vector of the present invention may be inserted into the chromosome by homologous recombination, it may further include a selection marker to confirm chromosomal insertion. The selection marker is to select cells that are transformed with the vector, that is, to confirm insertion of the desired polynucleotide, and the selection marker may include markers providing selectable phenotypes, such as drug resistance, auxotrophy, resistance to cytotoxic agents, or surface protein expression. Only cells expressing the selection marker are able to survive or to show different phenotypes under the environment treated with the selective agent, and thus the transformed cells may be selected.

As used herein, the term "transformation" means the introduction of a vector including a polynucleotide encoding a target protein into a host cell in such a way that the protein encoded by the polynucleotide is expressed in the host cell. As long as the transformed polynucleotide can be expressed in the host cell, it can be either integrated into and placed in the chromosome of the host cell, or exist extrachromosomally. Further, the polynucleotide includes DNA and RNA encoding the target protein. The polynucleotide may be introduced in any form, as long as it can be introduced into the host cell and expressed therein. For example, the polynucleotide may be introduced into the host cell in the form of an expression cassette, which is a gene construct including all elements required for its autonomous expression. Typically, the expression cassette includes a promoter operably linked to the polynucleotide, transcriptional termination signals, ribosome binding sites, or translation termination signals. The expression cassette may be in the form of a self-replicable expression vector. Also, the polynucleotide as it is may be introduced into the host cell and operably linked to sequences required for expression in the host cell.

Further, as used herein, the term "operably linked" means a functional linkage between a polynucleotide sequence encoding the desired protein of the present invention and a promoter sequence which initiates and mediates transcription of the polynucleotide sequence.

Further, the microorganism having diamine productivity may be a microorganism, in which the diamine acetyltransferase activity is weakened compared to the endogenous activity, in order to increase diamine production.

As used herein, the term "diamine acetyltransferase" is an enzyme catalyzing transfer of an acetyl group from acetyl-CoA to diamine, and it may be exemplified by *Corynebacterium* glutamicum NCgl1469 or *E. coli* SpeG, but its name may differ depending on the species of a microorganism having diamine productivity. NCgl1469 may have an amino acid sequence of SEQ ID NO: 11 or 12, and SpeG may have an amino acid sequence of SEQ ID NO: 13, but the sequence may differ depending on the species of the microorganism. The protein may have an amino acid sequence having 80% or higher, preferably 90% or higher, or more preferably 95% or higher, or particularly preferably 97% or higher homology therewith, as long as it has the diamine acetyltransferase activity.

Since the diamine acetyltransferase converts diamine to acetyl-diamine (e.g., N—Ac-putrescine or N—Ac-cadaverine), diamine productivity may be increased by weakening its activity, compared to the endogenous activity.

As used herein, the term "endogenous activity" refers to activity of the protein that the original microorganism possesses in its native or undenatured state, and "modified to have weakened activity, compared to the endogenous activity" means that activity of the protein is further weakened compared to the activity of the corresponding protein that the original microorganism possesses in the native or undenatured state.

The weakening of the protein activity means that the protein activity is reduced, compared to a non-modified strain, or the activity is eliminated. It is possible to apply a method well known in the art to the weakening of the protein activity.

Examples of the method may include a method of replacing the gene encoding the protein on the chromosome by a gene that is mutated to reduce the enzyme activity or to eliminate the protein activity, a method of introducing a mutation into the expression regulatory sequence of the gene encoding the protein on the chromosome, a method of replacing the expression regulatory sequence of the gene encoding the protein by a sequence having weaker activity, a method of deleting a part or an entire of the gene encoding the protein on the chromosome, a method of introducing antisense oligonucleotide that complementarily binds to a transcript of the gene on the chromosome to inhibit translation of mRNA to the protein, a method of artificially adding a sequence complementary to SD sequence at upstream of SD sequence of the gene encoding the protein to form a secondary structure, thereby preventing access of the ribosomal subunits, and a reverse transcription engineering (RTE) method of adding a promoter for reverse transcription at 3'-terminus of open reading frame (ORF) of the corresponding sequence, and combinations thereof, but are not particularly limited thereto.

In detail, a partial or full deletion of the gene encoding the protein may be done by introducing a vector for chromosomal insertion into a microorganism, thereby substituting the polynucleotide encoding an endogenous target protein on chromosome with a polynucleotide having a partial deletion or a marker gene. The "partial" may vary depending on the type of polynucleotide, but specifically refers to 1 to 300, preferably 1 to 100, and more preferably 1 to 50 nucleotides.

Meanwhile, the microorganism of the present invention is a microorganism having diamine productivity, and includes a prokaryotic microorganism expressing the protein having the amino acid sequence of SEQ ID NO: 6, and examples thereof may include microorganisms belonging to *Escherichia* sp., *Shigella* sp., *Citrobacter* sp., *Salmonella* sp., *Enterobacter* sp., *Yersinia* sp., *Klebsiella* sp., *Erwinia* sp., *Corynebacterium* sp., *Brevibacterium* sp., *Lactobacillus* sp., *Selenomanas* sp., *Vibrio* sp., *Pseudomonas* sp., *Streptomyces* sp., *Arcanobacterium* sp., *Alcaligens* sp. or the like, but are not limited thereto. The microorganism of the present invention is specifically a microorganism belonging to *Corynebacterium* sp. or *Escherichia* sp., and more specifically, *Corynebacterium* glutamicum or *Escherichia coli*, but is not limited thereto.

A specific example may be a microorganism prepared by deleting NCgl2522, which is a protein having putrescine export activity, from a *Corynebacterium* glutamicum ATCC13032-based putrescine-producing strain KCCM11240P (Korean Patent Publication No. 2013-0082478) and then introducing CE2495 into the transposon gene. Therefore, this microorganism KCCM11240P ΔNCgl2522 Tn:P (cj7)-CE2495 is designated as CC01-0757, and deposited under the Budapest Treaty to the Korean Culture Center of Microorganisms (KCCM) on Nov. 15, 2013, with Accession No. KCCM11475P.

In another aspect, the present invention provides a method of producing diamine, comprising: (i) culturing the microorganism having putrescine diamine, in which activity of the protein having the amino acid sequence of SEQ ID NO: 6 or 55% or higher sequence homology therewith is introduced or enhanced, so as to obtain a cell culture; and (ii) recovering diamine from the cultured microorganism or the cell culture.

The protein having the amino acid sequence of SEQ ID NO: 6 or the protein having the amino acid sequence having 55% or higher sequence homology therewith, the introduction of the protein activity, the enhancement of the protein activity, the diamine, and the microorganism having diamine productivity are the same as described above.

In the method, the step of culturing the microorganism may be, although not particularly limited to, preferably performed by batch culture, continuous culture, and fed-batch culture known in the art. In this regard, the culture conditions are not particularly limited, but an optimal pH (e.g., pH 5 to 9, preferably pH 6 to 8, and most preferably pH 6.8) may be maintained by using a basic chemical (e.g., sodium hydroxide, potassium hydroxide or ammonia) or acidic chemical (e.g., phosphoric acid or sulfuric acid). Also, an aerobic condition may be maintained by adding oxygen or oxygen-containing gas mixture to a cell culture. The culture temperature may be maintained at 20 to 45° C., and preferably at 25 to 40° C., and the cultivation may be performed for about 10 to 160 hours.

Furthermore, a medium to be used for culture may include sugar and carbohydrate (e.g., glucose, sucrose, lactose, fructose, maltose, molasse, starch and cellulose), oil and fat (e.g., soybean oil, sunflower seed oil, peanut oil and coconut oil), fatty acid (e.g., palmitic acid, stearic acid and linoleic acid), alcohol. (e.g., glycerol and ethanol), and organic acid (e.g., acetic acid) individually or in combination as a carbon source; nitrogen-containing organic compound (e.g., peptone, yeast extract, meat juice, malt extract, corn solution, soybean meal powder and urea), or inorganic compound (e.g., ammonium sulfate, ammonium, chloride, ammonium phosphate, ammonium carbonate, and ammonium nitrate) individually or in combination as a nitrogen source; potassium dihydrogen phosphate, dipotassium phosphate, or sodium-containing salt corresponding thereto individually or in combination as a phosphorus source; other essential growth-stimulating substances including metal salts (e.g., magnesium sulfate or iron sulfate), amino acids, and vitamins. In the present invention, the medium may be used as a synonym for the culture liquid.

As used herein, the term "cell culture" is a material obtained by culturing a microorganism, and includes the medium, the microorganism cultured, and substances released from the microorganism cultured. For example, a nutrient supply source required for cell culture, such as minerals, amino acids, vitamins, nucleic acids and/or other components generally contained in culture medium (or culture liquid) in addition to the carbon source, and the nitrogen source may be included. Further, a desired substance or an enzyme produced/secreted by the cells may be included.

Since diamine produced by culture may be secreted into the medium or remain in the cells, the cell culture may include diamine that is produced by culturing the microorganism.

The method of recovering diamine such as putrescine or cadaverine produced in the culturing step of the present invention may be carried out, for example, using a suitable method known in the art according to a culturing method, for example, batch culture, continuous culture, or fed-batch culture, thereby collecting the desired amino acids from the culture liquid.

Advantageous Effects

In the present invention, it is demonstrated that *Corynebacterium efficiens*-derived CE2495 protein is a protein having diamine export activity, and putrescine export activity can be enhanced by introducing this protein activity into *Corynebacterium* sp. microorganism which has a putrescine synthetic pathway, but low putrescine export activity. It is also demonstrated that putrescine and cadaverine can be increased at the same time by introducing this protein activity into *E. coli* which has synthetic pathways of putrescine and cadaverine. Accordingly, diamine can be effectively produced by applying *Corynebacterium efficiens*-derived CE2495 protein to a microorganism having diamine productivity.

MODE FOR INVENTION

Hereinafter, the present invention will be described in more detail with reference to Examples. However, these Examples are for illustrative purposes only, and the invention is not intended to be limited by these Examples.

Reference Example 1

Preparation of *Corynebacterium* sp. Microorganism Having Putrescine Productivity It was confirmed that putrescine production was reduced when NCgl2522, a permease belonging to major facilitator superfamily (MFS), was deleted in a *Corynebacterium* glutamicum ATCC13032-based putrescine-producing strain KCCM11240P (Korean Patent Publication NO. 2013-0082478) and a *Corynebacterium* glutamicum ATCC13869-based putrescine-producing strain DAB12-a ΔNCgl1469 (argF deletion, NCgl1221 deletion, *E. coli* speC introduction, arg operon promoter substitution, NCgl1469 deletion; designated as DAB12-b, Korean Patent Publication No. 2013-0082478) as *Corynebacterium* sp. microorganisms having putrescine productivity.

It was also confirmed that putrescine was produced in a high yield in *Corynebacterium* glutamicum strains prepared by additional introduction of NCgl2522 gene into the transposon in KCCM11240P or DAB12-b, or by substitution of NCgl2522 promoter on the chromosome with cj7 promoter to enhance NCgl2522 activity. Further, the intracellular amount of putrescine was measured in the strain in which NCgl2522 expression was enhanced, and as a result, a smaller amount of putrescine was observed, compared to that of a control group. It is indicating that NCgl2522 has an ability to export putrescine.

In detail, based on the nucleotide sequence of the gene encoding NCgl2522 of *Corynebacterium* glutamicum ATCC13032, a pair of primers of SEQ ID NOS: 1 and 2 for obtaining a homologous recombination fragment of the N-terminal region of NCgl2522 and a pair of primers of SEQ ID NOS: 3 and 4 for obtaining a homologous recombination fragment of the C-terminal region of NCgl2522 were used as in the following Table 1.

TABLE 1

| Primer | Sequence (5'->3') |
|---|---|
| NCgl2522-del-F1_BamHI (SEQ ID NO: 1) | CGGGATCCCACGCCTGTCTGGTCGC |
| NCgl2522-del-R1_SalI (SEQ ID NO: 2) | ACGCGTCGACGGATCGTAACTGTAACGAATGG |
| NCgl2522-del-F2_SalI (SEQ ID NO: 3) | ACGCGTCGACCGCGTGCATCTTTGGACAC |
| NCgl2522-del-R2_XbaI (SEQ ID NO: 4) | CTAGTCTAGAGAGCTGCACCAGGTAGACG |

PCR was performed using the genomic DNA of *Corynebacterium glutamicum* ATCC13032 as a template and two pairs of primers so as to amplify PCR fragments of the N-terminal and C-terminal regions, respectively. These PCR fragments were electrophoresed to obtain the desired fragments. At this time, PCR reaction was carried out for 30 cycles of denaturation for 30 seconds at 95° C., annealing for 30 seconds at 55° C., and extension for 30 seconds at 72° C. The fragment of the N-terminal region thus obtained was treated with restriction enzymes, BamHI and SalI and the fragment of the C-terminal region thus obtained was treated with restriction enzymes, SalI and XbaI. The fragments thus treated, were cloned into the pDZ vector treated with restriction enzymes, BamHI and XbaI, so as to construct a plasmid pDZ-1'NCgl2522 (K/O).

The plasmid pDZ-1'NCgl2522(K/O) was introduced into *Corynebacterium glutamicum* KCCM11240P by electroporation, so as to obtain a transformant. Then, the transformant was plated and cultured on BHIS plate (37 g/l of Braine heart infusion, 91 g/l of sorbitol, and 2% agar) containing kanamycin (25 μg/ml) and X-gal (5-bromo-4-chloro-3-indolin-D-galactoside) for colony formation. From the colonies thus formed, blue-colored colonies were selected as the strain introduced with the plasmid pDZ-1'NCgl2522(K/O).

The selected strains were cultured with shaking in CM medium (10 g/l of glucose, 10 g/l of polypeptone, 5 g/l of yeast extract, 5 g/l of beef extract, 2.5 g/l of NaCl, and 2 g/l of urea, pH 6.8) at 30° C. for 8 hours. Subsequently, each cell culture was serially diluted from $10^{-4}$ to $10^{-10}$. Then, the diluted samples were plated and cultured on an X-gal-containing solid medium for colony formation. From the colonies thus formed, the white colonies which appeared at relatively low frequency were selected, to finally obtain a *Corynebacterium glutamicum* strain in which the gene encoding NCgl2522 was deleted and putrescine productivity was weakened. The *Corynebacterium glutamicum* strain in which putrescine export activity was weakened was designated as KCCM11240P ΔNCgl2522.

In the same manner, PCR was performed using the genomic DNA of *Corynebacterium glutamicum* ATCC13869 as a template and two pairs of primers given in Table 1 so as to construct a plasmid pDZ-2'NCgl2522(K/O) by the above described method. A *Corynebacterium glutamicum* strain, in which the gene encoding NCgl2522 of DAB12-b strain was deleted using the vector according to the above described method to weaken putrescine productivity, was constructed. This *Corynebacterium glutamicum* strain having weakened putrescine export activity was designated as DAB12-b ΔNCgl2522.

Example 1. Selection of *Corynebacterium efficiens* CE2495

As confirmed in Reference Example 1, the NCgl2522 membrane protein was found to function to export putrescine. Therefore, based on the amino acid sequence of NCgl2522, the present inventors acquired genes having homology therewith using BlastP program of National Center for Biotechnology Information (NCBI, www.ncbi.nlm.nih.gov).

From *Corynebacterium* sp. other than *Corynebacterium glutamicum*, *Corynebacterium efficiens* YS-314 was found to have CE2495 which shows 71% homology with the amino acid sequence of NCgl2522. Its nucleotide sequence (SEQ ID NO: 5) and amino acid sequence (SEQ ID NO: 6) were obtained.

In the same manner, the nucleotide sequence (SEQ ID NO: 21) and amino acid sequence (SEQ ID NO: 22) of HMPREF0281_01446 derived from *Corynebacterium ammoniagenes* DSM 20306, which shows 59% homology with the amino acid sequence of NCgl2522, and the nucleotide sequence (SEQ ID NO: 23) and amino acid sequence (SEQ ID NO: 24; of HMPREF0298_0262 derived from *Corynebacterium lipophiloflavum* DSM 44291, which shows 52% homology with the amino acid sequence of NCgl2522, were obtained. The amino acid sequence of HMPREF0281_01446 and the amino acid sequence of HMPREF0298_0262 show 61% and 56% homology with the amino acid sequence of CE2495 of *Corynebacterium efficiens* YS-314, respectively, as shown in the following Table 2.

TABLE 2

Comparison of amino acid sequence homology

| | CE2495 (SEQ ID NO: 6) | HMPREF0281_01446 (SEQ ID NO: 22) | HMPREF0298_0262 (SEQ ID NO: 24) |
|---|---|---|---|
| NCgl2522 | 71% | 59% | 52% |
| CE2495 | | 61% | 56% |

Meanwhile, *Corynebacterium* sp. microorganisms having genes showing homology with NCgl2522, and homology thereof are given in the following Table 3.

TABLE 3

| Species | Homology |
|---|---|
| *Corynebacterium accolens* | 53% |
| *Corynebacterium ammoniagenes* | 59% |
| *Corynebacterium amycolatum* | 59% |
| *Corynebacterium atypicum* | 56% |
| *Corynebacterium aurimucosum* | 58% |
| *Corynebacterium auriscanis* | 53% |
| *Corynebacterium callunae* | 73% |
| *Corynebacterium camporealensis* | 56% |
| *Corynebacterium capitovis* | 56% |
| *Corynebacterium casei* | 60% |
| *Corynebacterium casei* LMG S-19264 | 60% |
| *Corynebacterium caspium* | 57% |
| *Corynebacterium diphtheriae* | 56% |
| *Corynebacterium efficiens* | 71% |
| *Corynebacterium falsenii* DSM 44353 | 51% |
| *Corynebacterium genitalium* | 55% |
| *Corynebacterium glutamicum* 13032 | 100% |
| *Corynebacterium glutamicum* R | 100% |
| *Corynebacterium glutamicum* 13869 | 99% |
| *Corynebacterium glutamicum* ATCC 14067 | 97% |
| *Corynebacterium glycinophilum* AJ 3170 | 59% |
| *Corynebacterium halotolerans* | 65% |
| *Corynebacterium jeikeium* | 46% |
| *Corynebacterium lipophiloflavum* | 52% |
| *Corynebacterium maris* | 58% |
| *Corynebacterium massiliense* | 54% |
| *Corynebacterium mastitidis* | 56% |

TABLE 3-continued

| Species | Homology |
|---|---|
| Corynebacterium matruchotii | 58% |
| Corynebacterium nuruki | 59% |
| Corynebacterium pilosum | 55% |
| Corynebacterium pseudodiphtheriticum | 51% |
| Corynebacterium pseudogenitalium | 53% |
| Corynebacterium pseudotuberculosis | 59% |
| Corynebacterium resistens | 52% |
| Corynebacterium sp. ATCC 6931 | 59% |
| Corynebacterium sp. HFH0082 | 59% |
| Corynebacterium sp. KPL1818 | 53% |
| Corynebacterium sp. KPL1824 | 53% |
| Corynebacterium striatum | 57% |
| Corynebacterium terpenotabidum | 58% |
| Corynebacterium tuberculostearicum | 53% |
| Corynebacterium tuscaniense DNF00037 | 53% |
| Corynebacterium ulcerans | 62% |
| Corynebacterium urealyticum | 51% |
| Corynebacterium ureicelerivorans | 52% |
| Corynebacterium variabile | 56% |
| Corynebacterium vitaeruminis DSM 20294 | 54% |

Example 2. Fermentation of Putrescine by Introduction of CE2495 into Putrescine-Producing Strain Derived from Corynebacterium sp.

<2-1> Introduction of CE2495 into Transposon Gene in Chromosome of ATCC13032-Based Putrescine-Producing Strain In order to examine whether chromosomal insertion of CE2495 gene affects putrescine export in KCCM11240P ΔNCgl2522 having reduced putrescine export activity which was prepared in Reference Example 1, CE2495 was introduced into a transposon gene by the following method.

As a vector for transformation, which allows a gene insertion into the chromosome using a transposon gene of Corynebacterium sp. microorganism, pDZTn (WO 2009/125992) was used, and cj7 (WO 2006/65095) was used as a promoter.

A CE2495 gene fragment of about 1.44 kb was amplified using the chromosome of Corynebacterium efficiens YS-314 strain as a template and a pair of primers of SEQ ID NOS: 9 and 10 (See Table 4). At this time, PCR reaction was carried out for 30 cycles of denaturation for 30 seconds at 95° C., annealing for 30 seconds at 55° C., and extension for 1 minute and 30 seconds at 72° C. Next, this PCR product was electrophoresed on a 0.8% agarose gel to elute and purify a band of the desired size.

Further, the cj7 promoter region was obtained by carrying out PCR for 30 cycles of denaturation for 30 seconds at 95° C., annealing for 30 seconds at 55° C., and extension for 30 seconds at 72° C. using p117-Pcj7-gfp as a template and a pair of primers of SEQ ID NOs. 7 and 8 (See Table 4). A fragment of the cj7 promoter gene was electrophoresed on a 0.8% agarose gel to elute and purify a band of the desired size.

TABLE 4

| Primer | Sequence (5'->3') |
|---|---|
| CJ7-F (SEQ ID NO: 7) | TGTCGGGCCCACTAGTAGAAACATCCCAGCGC TACTAATA |
| CJ7-R (SEQ ID NO: 8) | AGTGTTTCCTTTCGTTGGGTACG |
| CE2495-F (SEQ ID NO: 9) | CAACGAAAGGAAACACTATGAATCCCACAGC- CTCGC |
| CE2495-R (SEQ ID NO: 10) | GAATGAGTTCCTCGAG TCACCCGGGGCGCTTCG | pDZTn vector was treated with XhoI, and fusion cloning of the PCR product obtained above was performed. In-Fusion@HD Cloning Kit (Clontech) was used in the fusion cloning. The resulting plasmid was designated as pDZTn-P(cj7)-CE2495.

Next, the plasmid pDZTn-P(cj7)-CE2495 was introduced into Corynebacterium glutamicum KCCM11240P ΔNCgl2522 described in Reference Example 1 by electroporation to obtain a transformant. The transformant was cultured with shaking in CM medium (10 g/l of glucose, 10 g/l of polypeptone, 5 g/l of yeast extract, 5 g/l of beef extract, 2.5 g/l of NaCl, and 2 g/l of urea, pH 6.8) (30° C. for 8 hours). Subsequently, cell culture was serially diluted from $10^{-4}$ to $10^{-10}$. Then, the diluted samples were plated and cultured on an X-gal-containing solid medium for colony formation.

From the colonies formed, the white colonies which appeared at relatively low frequency were selected to finally obtain strains in which the gene encoding CE2495 was introduced by secondary crossover. The strains finally selected were subjected to PCR using a pair of primers of SEQ ID NOS: 7 and 10 to confirm introduction of the gene encoding CE2495. This Corynebacterium glutamicum mutant strain was designated as KCCM11240P ΔNCgl2522 Tn:P(cj7)-CE2495.

<2-2> Introduction of CE2495 into Transposon Gene in Chromosome of ATCC13869-Based Putrescine-Producing Strain In order to examine whether the chromosomal insertion of CE2495 gene affects putrescine export in DAB12-b ΔNCgl2522 having reduced putrescine export activity which was prepared in Reference Example 1, pDZTn-P(cj7)-CE2495 prepared above was introduced into Corynebacterium glutamicum DAB12-ΔNCgl2522 and strain is confirmed introduction of CE2495 into the transposon gene in the same manner as in Example <2-1>.

A Corynebacterium glutamicum mutant strain thus selected was designated as DAB12-b ΔCgl2522 Tn:P(cj7)-CE24 95.

<2-3> Evaluation of Putrescine Productivity of Corynebacterium sp.-Derived Putrescine-Producing Strain Introduced with CE2495

In order to confirm the effect of CE2495 introduction on putrescine productivity in the putrescine-producing strain, putrescine productivities of the Corynebacterium glutamicum mutant strains prepared in Examples <2-1> and <2-2> were compared.

In detail, 6 types of Corynebacterium glutamicum mutants (KCCM11240P; KCCM11240P ΔNCgl2522; KCCM11240P ΔNCgl2522 Tn:P(cj7)-CE2495; DAB12-b; DAB12-b ΔNCgl2522; DAB12-b ΔNCgl2522 Tn:P (cj7)-CE2495) were plated, on 1 mM arginine-containing CM plate media (1% glucose, 1% polypeptone, 0.5% yeast extract, 0.5% beef extract, 0.25% NaCl, 0.2% urea, 100 μl of 50% NaOH, and 2% agar, pH 6.8, based on 1 L), and cultured at 30° C. for 24 hours, respectively. 1 platinum loop of each strain thus cultured was inoculated in 25 ml of titer medium (8% Glucose, 0.25% soybean protein, 0.50% corn steep solids, 4% (NH$_4$)$_2$SO$_4$, 0.1% KH$_2$PO$_4$, 0.05% MgSO$_4$·7H$_2$O, 0.15% urea, 100 µg of biotin, 3 mg of thiamine hydrochloride, 3 mg of calcium-pantothenic acid, 3 mg of nicotinamide, and 5% CaCO$_3$, pH 7.0, based on 1 L), and then cultured with shaking at 30° C. and 200 rpm for 98 hours. 1 mM arginine was added to all media for culturing the strains. The putrescine concentration in each cell culture was measured, and the results are shown in the following Table 5.

TABLE 5

| Strain | Putrescine (g/L) |
|---|---|
| KCCM 11240P | 12.4 |
| KCCM 11240P ΔNCgl2522 | 1.9 |
| KCCM 11240P ΔNCgl2522 Tn:P(cj7)-CE2495 | 17.8 |
| DAB12-b | 13.1 |
| DAB12-b ΔNCgl2522 | 0.5 |
| DAB12-b ΔNCgl2522 Tn:P(cj7)-CE2495 | 17.9 |

As shown in Table 5, putrescine production was found to be increased in both 2 types of the CE2495-introduced *Corynebacterium* glutamicum mutant strains.

Example 3. Fermentation of Cadaverine by CE2495 Introduction and Lysine Decarboxylase Expression in *Corynebacterium* sp.-Derived Lysine-Producing Strain <3-1> Introduction of CE2495 into Transposon Gene in Chromosome of L-Lysine-Producing *Corynebacterium* Glutamicum KCCM11016P In order to confirm cadaverine export activity of CE2495 protein, CE2495 gene was introduced into the chromosome of a lysine-producing strain KCCM11016P (this microorganism was deposited at the Korean Culture Center of Microorganisms on Dec. 18, 1995 with Accession No. KFCC10881, and then deposited at the International Depository Authority under Budapest Treaty with Accession No. KCCM11016P, Korean Patent No. 10-0159812). pDZTn-P (cj7)-CE2495 prepared above was introduced into *Corynebacterium* glutamicum KCCM11016P and strain is confirmed introduction of CE2495 into transposon in the same manner as in Example <2-1>.

A *Corynebacterium* glutamicum mutant strain thus selected was designated as KCCM11016P Tn:P (cj7)-CE2495.

<3-2> Introduction of *E. Coli*-Derived Lysine Decarboxylase Gene into L-Lysine-Producing Strain Introduced CE2495

The L-lysine-producing strain introduced CE2495, KCCM11016P Tn:P (cj7)-CE2495 which was prepared in Example <3-1> was introduced with *E. coli*-derived lysine decarboxylase gene in a plasmid form for cadaverine production. The nucleotide sequence (SEQ ID NO; 25) and amino acid sequence (SEQ ID NO: 26) of lysine decarboxylase ldcC were obtained from NCBI data base.

An ldcC gene fragment of about 2.1 kb was obtained by carrying out PCR for 30 cycles of denaturation for 30 seconds at 95° C., annealing for 30 seconds at 52° C., and extension for 2 minutes at 72° C. using the chromosome of *E. coli* W3110 strain as a template and a pair of primers of SEQ ID NOS: 29 and 30 (See Table 6). This product was treated with HindIII and XbaI, and then electrophoresed in a 0.8% agarose gel to elute and purify a band of the desired size.

Further, the cj7 promoter region was obtained by carrying out PCR for 30 cycles of denaturation for 30 seconds at 95° C., annealing for 30 seconds at 55° C., and extension for 30 seconds at 72° C. using p117-Pcj7-gfp as a template and a pair of primers of SEQ ID NOs. 27 and 28 (See Table 6). A gene fragment of the cj7 promoter gene was treated with KpnI and HindII, and then electrophoresed on a 0.8% agarose gel to elute and purify a band of the desired size.

TABLE 6

Primer for promoter cj7 gene

| | |
|---|---|
| CJ7-F_KpnI (SEQ ID NO: 27) | CGGGGTACC AGAAACATCCCAGCGCTACTAATA |
| CJ7-R-HindIII (SEQ ID NO: 28) | CCCAAGCTT AGTGTTTCCTTTCGTTGGGTACG |

Primer for *E. coli* ldcC gene

| | |
|---|---|
| ldcC-F_HindIII (SEQ ID NO: 29) | CCCAAGCTT AAGCTT ATGAACATCATTGCCATTATGGG (52) |
| ldcC-R_XbaI (SEQ ID NO: 30) | TGCTCTAGA TTATCCCGCCATTTTTAGGACTC (53) |

A gene fragment which was obtained by performing electrophoresis of KpnI and XbaI-treated pECCG117 (Biotechnology letters vol 13, No. 10, p. 721-726 (1991)) vector in a 0.8% agarose gel and then eluting and purifying a band of the desired size, the cj7 promoter gene fragment treated with KpnI and HindIII, and the lysine decarboxylase ldcC gene fragment treated with HindIII and XbaI were cloned using T4 DMA ligase (NEB). The *E. coli* ldcC-encoding plasmid obtained by the above experiment was designated as pECCG117-Pcj7-ldcC.

The prepared pECCG117-Pcj7-ldcC vector or pECCG117 vector was introduced into KCCM11016P and KCCM11016P Tn:P (cj7)-CE2495 by electroporation, respectively. The transformants were plated on BHIS plate containing 25 µg/ml kanamycin for selection. The selected strains were designated as KCCM11016P pECCG117, KCCM11016P pECCG117-Pcj7-ldcC, KCCM11016P Tn:P (cj7)-CE2495 pECCG117, and KCGM11016P Tn:P(cj7)-CE2495 pECCG117-Pcj7-ldcC, respectively.

<3-3> Evaluation of Cadaverine Productivity of *Corynebacterium* sp.-Derived Lysine-Producing Strain Having Chromosomal Insertion of CE2495 and Lysine Decarboxylase Gene as Plasmid In order to examine whether introduction of CE2495 into the cadaverine-producing strain affects cadaverine production, cadaverine productivity was compared between *Corynebacterium* glutamicum mutant strains prepared in Example <3-2>.

In detail, 4 types of *Corynebacterium* glutamicum mutant strains (KCCM11016P pECCG117; KCCM11016P pECCG117-Pcj7-ldcC; KCCM11016P Tn:P(cj7)-CE2495 pECCG117; and KCCM11016P Tn:P(cj7)-CE2495 pECCG117-Pcj7-ldcC) were cultured by the following method, and cadaverine productivity was compared therebetween.

The respective mutant strains were plated on CM plate media (1% glucose, 1% polypeptone, 0.5% yeast extract, 0.5% beef extract, 0.25% NaCl, 0.2% urea, 100 µl of 50% NaOH, and 2% agar, pH 6.8, based on 1 L), and cultured at 30° C. for 24 hours. Each of the strains cultured was inoculated to a 250 ml corner-baffled flask containing 25 ml of seed medium (2% glucose, 1% peptone, 0.5% yeast extract, 0.15% urea, 0.4% KH$_2$PO$_4$, 0.8% K$_2$HPO$_4$, 0.05% MgSO$_4$ 7H$_2$O, 100 µg of biotin, 1000 µg of thiamine HCl, 2000 μg of calcium-pantothenic acid, and 2000 μg of nicotinamide, pH 7.0, based on 1 L), and cultured with shaking at 30° C. and 200 rpm for 20 hours.

Then, 1 ml of the seed culture was inoculated to a 250 ml corner-baffled flask containing 24 ml of production medium (4% Glucose, 2% $(NH_4)_2SO_4$, 2.5% soybean protein, 5% corn steep solids, 0.3% urea, 0.1% $KH_2PO_4$, 0.05% $MgSO_4$ $7H_2O$, 100 μg of biotin, 1000 μg of thiamine hydrochloride, 2000 μg of calcium-pantothenic acid, 3000 μg of nicotinamide, 0.2 g of leucine, 0.1 g of threonine, 0.1 g of methionine, and 5% $CaCO_3$, pH 7.0, based on 1 L), and then cultured with shaking at 30° C. and 200 rpm for 72 hours.

After culture, cadaverine productivities were measured by HPLC. The concentrations of cadaverine in the cell culture of each strain are given in the following Table 7.

TABLE 7

| Strain | Plasmid | Cadaverine (g/L) |
|---|---|---|
| KCCM11016P | pECCG117 | 0 |
|  | pECCG117-Pcj7-ldcC | 2.3 |
| KCCM11016P Tn:P(cj7)-CE2495 | pECCG117 | 0 |
|  | pECCG117-Pcj7-ldcC | 3.3 |

As shown in Table 7, cadaverine production was increased in the CE2495-introduced *Corynebacterium glutamicum* mutant strains.

Example 4. Fermentation of Diamine by Introduction of Protein Having Diamine Export Activity into *E. Coli*

<4-1> Preparation of Strain by Introduction of CE2495, HMPREF0281_01446, or HMPREF0298_0262 into W3110

The diamine export activities of *Corynebacterium ammoniagenes* DSM 20306-derived HMPREF0281_01446 protein and HMPREF0298_0262 protein, which show 59% and 52% homology with NCgl2522, in addition to CE24952, respectively, were examined in *E. coli*.

Vectors for introduction of HMPREF0281_01446 and HMPREF0281_01446 were constructed in the same manner as in the construction of pDZTn-P(cj7)-CE2495 of Example 2-1.

HMPREF0281_01446 gene was amplified using the chromosome of *Corynebacterium ammoniagenes* DSM 20306 strain as a template and a pair of primers of SEQ ID NOS: 31 and 32 (see Table 8) so as to obtain a gene fragment of about 1.4 kb.

In the same manner, HMPREF0298_0262 gene was amplified using the chromosome of *Corynebacterium lipophiloflavum* DSM 44291 strain as a template and a pair of primers of SEQ ID NOS: 33 and 34 (see Table 8) so as to obtain a gene fragment of about 1.36 kb.

In this regard, PCR was carried out for 30 cycles of denaturation for 30 seconds at 95° C., annealing for 30 seconds at 55° C., and extension for 1 minute and 30 seconds at 72° C. Then, each of the PCR products was electrophoresed on a 0.8% agarose gel to elute and purify a band of the desired size.

TABLE 8

| Primer | Sequence (5'->3') |
|---|---|
| CJ7-F (SEQ ID NO: 7) | TGTCGGGCCCACTAGTAGAAACATCCCAG CGCTACTAATA |

TABLE 8-continued

| Primer | Sequence (5'->3') |
|---|---|
| CJ7-R (SEQ ID NO: 8) | AGTGTTTCCTTTCGTTGGGTACG |
| HMPREF0281_01446-F (SEQ ID NO: 31) | CAACGAAAGGAAACACTATGATTGGCTTG GATAACTCCATC |
| HMPREF0281_01446-R (SEQ ID NO: 32) | GAATGAGTTCCTCGAG TTACTCGTCCGC GCCACC |
| HMPREF0298_2062-F (SEQ ID NO: 33) | CAACGAAAGGAAACACT ATGCGTTGGTT GCTTCTCGG |
| HMPREF0298_0262-R (SEQ ID NO: 34) | GAATGAGTTCCTCGAG CTAACTGCGCTG GTGGGC |

Further, the cj7 promoter region was obtained by carrying out PCR for 30 cycles of denaturation for 30 seconds at 95° C., annealing for 30 seconds at 55° C., and extension for 30 seconds at 72° C. using p117-Pcj7-gfp as a template and a pair of primers of SEQ ID NOS: 7 and 8. A fragment of the cj7 promoter gene was electrophoresed on a 0.8% agarose gel to elute and purify a band of the desired size.

pDZTn vector was treated with XhoI, and fusion cloning of the PCR products obtained above was performed. In-Fusion@HD Cloning Kit (Clontech) was used in the fusion cloning. The resulting plasmids were designated as pDZTn-P (cj7)-HMPREF0281_01446 and pDZTn-P(cj7)-HMPREF029_0262, respectively.

Thereafter, in order to examine whether expression of *Corynebacterium efficiens* YS-314-derived CE2495, *Corynebacterium ammoniagenes*-derived HMPREF0281_01446, or *Corynebacterium lipophiloflavum*-derived HMPREF0298_0262 protein increases putrescine and cadaverine productions in *E. coli* wild-type strain W3110 having biosynthetic pathway of putrescine and cadaverine, *Corynebacterium* and *E. coli* shuttle vector-based pDZTn-P (cj7)-CE2495, pDZTn-P (cj7)-HMPREF0281_01446, or pDZTn-P (cj7)-HMPREF0298_0262 was introduced into W3110, respectively.

A 2×TSS solution (Epicentre) was used for transformation into *E. coli*, and the transformant was plated and cultured on LB plate (10 g of Tryptone, 5 g of Yeast extract, 10 g of NaCl, and 2% agar, based on 1 L) containing kanamycin (50 μg/ml) for colony formation. The colonies thus formed were designated as W3110 pDZTn-P(cj7)-CE2495, W3110 pDZTn-P(cj7)-HMPREF0281_01446, and W3110 pDZTn-P (cj7)-HMPREF0298_0262, respectively.

<4-2> Comparison of Diamine Productivity of *E. coli* Introduced with CE2495, HMPREF0281_01446, or HMPREF0298_0262

Putrescine and cadaverine productivities of the strains obtained above were examined.

In detail, *E. coli* W3110 and W3110 pDZTn-P(cj7)-CE2495, W3110 pDZTn-P (cj7)-HMPREF0281_01446, or W3110 pDZTn-P(cj7)-HMPREF0298_0262 were cultured on LB solid media at 37° C. for 24 hours.

Then, each of them was cultured in 25 ml of titer medium (2 g of $(NH_4)_2PO_4$, 6.75 g of $KH_2PO_4$, 0.85 g of citric acid, 0.7 g of $MgSO_4.7H_2O$, 0.5% (v/v) trace element, 10 g of glucose, 3 g of AMS, and 30 g of $CaCO_3$, based on 1 L) at 37° C. for 24 hours. A trace metal solution contained 5 M HCl: 10 g of $FeSO_4.7H_2O$, 2.25 g of $ZnSO_4.7H_2O$, 1 g of $CuSO_4.5H_2O$, 0.5 g of $MnSO_4.5H_2O$, 0.23 g of $Na_2B_4O_7.10H_2O$, 2 g of $CaCl_2.2H_2O$, and 0.1 g of $(NH_4)_6Mo_7O_2.4H_2O$ per 1 liter.

The concentrations of putrescine and cadaverine produced from each cell culture were measured, and the results are given in the following Table 9.

TABLE 9

| Parent strain | Plasmid | Putrescine (mg/L) | Cadaverine (mg/L) |
|---|---|---|---|
| W3110 | (—) | 13 | 5 |
| | pDZTn-P(cj7)-CE2495 | 212 | 50 |
| | pDZTn-P(cj7)-HMPREF0281_01446 | 175 | 42 |
| | pDZTn-P(cj7)-HMPREF0298_0262 | 144 | 33 |

As shown in Table 9, CE2495-introduced W3110 pDZTn-P(cj7)-CE2495 strain showed high putrescine and cadaverine concentrations in ceil culture, compared to the parent strain W3110. Further, putrescine and cadaverine productions were remarkably increased in W3110 pDZTn-P (cj7)-HMPREF0281_01446 and W3110 pDZTn-P (cj7)-HMPREF0298_0262 strains which were introduced with HMPREF0281_01446 and HMPREF0298_0262, respectively.

That is, it was confirmed that diamine in cell culture was remarkably increased by enhancing activity of CE2495 or the protein having 55% or higher sequence homology therewith, suggesting that the ability to export diamine such as putrescine and cadaverine can be improved by enhancing activity of CE2495 or the protein having 55% or higher sequence homology therewith.

As such, the present inventors demonstrated that *Corynebacterium glutamicum* having enhanced CE2495 activity prepared by introducing CE2495 into transposon of *Corynebacterium* sp. microorganism KCCM11240P ΔNCgl2522 which has a putrescine synthetic pathway, but reduced putrescine export activity has enhanced putrescine export activity, thereby producing putrescine in a high yield.

Accordingly, this strain KCCM11240P ΔNCgl2522 Tn:P(cj7)-CE2495 was designated as CC01-0757, and deposited under the Budapest Treaty to the Korean Culture Center of Microorganisms (KCCM) on Nov. 15, 2013, with Accession No. KCCM11475P.

The invention claimed is:

1. A microorganism for producing putrescine, wherein a gene encoding a protein having an amino acid sequence of SEQ ID NO: 6, SEQ ID NO: 22 or SEQ ID NO: 24 is introduced.

2. The microorganism according to claim 1, wherein additionally activity of a diamine acetyltransferase is weakened, compared to the endogenous activity, wherein the weakened activity is achieved by one or more method(s) selected from the group consisting of:
   i) replacing the gene encoding the diamine acetyltransferase on the chromosome by a gene that is mutated to reduce the diamine acetyltransferase activity or to eliminate the diamine acetyltransferase activity;
   ii) introducing a mutation into the expression regulatory sequence of the gene encoding the diamine acetyltransferase on the chromosome;
   iii) replacing the expression regulatory sequence of the gene encoding the diamine acetyltransferase by a sequence having weaker activity;
   iv) deleting a part or an entire of the gene encoding the diamine acetyltransferase on the chromosome;
   v) introducing antisense oligonucleotide that complementarily binds to a transcript of the gene encoding diamine acetyltransferase on the chromosome to inhibit translation of mRNA to the diamine acetyltransferase;
   vi) artificially adding a sequence complementary to SD sequence at upstream of SD sequence of the gene encoding the diamine acetyltransferase to form a secondary structure, thereby preventing access of the ribosomal subunits; and
   vii) adding a promoter for reverse transcription at 3'-terminus of open reading frame (ORF) of the corresponding sequence encoding the diamine acetyltransferase.

3. The microorganism according to claim 2, wherein the diamine acetyltransferase has an amino acid sequence selected from the group consisting of SEQ ID NOS: 11, 12 and 13.

4. The microorganism according to claim 1, wherein the microorganism is a microorganism belonging to genus *Corynebacterium* or genus *Escherichia*.

5. A method of producing putrescine, comprising:
  (i) culturing the microorganism of claim 1 to obtain a cell culture; and
  (ii) recovering putrescine from the cultured microorganism or the cell culture.

6. The microorganism according to claim 1, wherein the microorganism already has an ability of producing putrescine before the gene is introduced.

7. The method according to claim 5, wherein the microorganism already has an ability of producing putrescine before the gene is introduced.

* * * * *